ns011676713B2

United States Patent
Huang et al.

(10) Patent No.: US 11,676,713 B2
(45) Date of Patent: Jun. 13, 2023

(54) DATA PROCESSING SYSTEM FOR CLASSIFYING KEYED DATA REPRESENTING INHALER DEVICE OPERATION

(71) Applicant: Carnegie Mellon University, Pittsburgh, PA (US)

(72) Inventors: Po-yao Huang, Pittsburgh, PA (US); Alexander G. Hauptmann, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 346 days.

(21) Appl. No.: 16/769,934

(22) PCT Filed: Dec. 5, 2018

(86) PCT No.: PCT/US2018/064087
§ 371 (c)(1),
(2) Date: Jun. 4, 2020

(87) PCT Pub. No.: WO2019/113222
PCT Pub. Date: Jun. 13, 2019

(65) Prior Publication Data
US 2020/0381111 A1    Dec. 3, 2020

Related U.S. Application Data

(60) Provisional application No. 62/708,345, filed on Dec. 5, 2017.

(51) Int. Cl.
*G08B 21/04*     (2006.01)
*G16H 40/63*     (2018.01)
(Continued)

(52) U.S. Cl.
CPC ........ *G16H 40/63* (2018.01); *A61M 15/0001* (2014.02); *A61M 15/009* (2013.01);
(Continued)

(58) Field of Classification Search
USPC ............ 340/539.12, 539.11, 539.22, 539.23, 340/539.13, 568.1, 588, 636.11, 691.1,
(Continued)

(56) References Cited

U.S. PATENT DOCUMENTS

| 6,958,691 B1 | 10/2005 | Anderson et al. |
| 8,660,971 B2 * | 2/2014 | Orr ........................ G16H 50/20 706/20 |

(Continued)

FOREIGN PATENT DOCUMENTS

| TW | 201820279 | 6/2018 |
| WO | WO 2018065883 | 4/2018 |

OTHER PUBLICATIONS

Bolton et al., "The cost and effectiveness of an education program for adults who have asthma," Journal of General Internal Medicine, 1991, 6(5):401-7.

(Continued)

*Primary Examiner* — Daniel Previl
(74) *Attorney, Agent, or Firm* — Fish & Richardson P.C.

(57) ABSTRACT

A data processing system digitally processes data feeds of inhaler device operation. The data feed represents operation of an inhaler device. The system indexes the live data feed with a key value representing the inhaler device for which the live data feed is obtained. For a particular key value indexed in the in-memory data storage, the system queries, a data feed representing physical operation of an inhaler device, segments the live data feed for that particular key value into a plurality of data samples, process at least a portion of the data samples to classify each of the processed (Continued)

data samples; outputs a prompt specifying whether operation of the inhaler device is within a threshold range of operation. Audio data, temperature data, image data, and ranging data can be processed to classify operation of the inhaler device and the order of operations of the inhaler device.

20 Claims, 17 Drawing Sheets

(51) Int. Cl.
  *A61M 15/00* (2006.01)
  *G16H 20/13* (2018.01)
(52) U.S. Cl.
  CPC ..... *G16H 20/13* (2018.01); *A61M 2205/3368* (2013.01); *A61M 2205/3561* (2013.01); *A61M 2205/581* (2013.01); *A61M 2205/583* (2013.01)
(58) Field of Classification Search
  USPC .......................................... 340/691.6, 825.25
  See application file for complete search history.

(56) References Cited

U.S. PATENT DOCUMENTS

| | | | |
|---|---|---|---|
| 10,437,962 B2* | 10/2019 | Soni | G16H 20/10 |
| 11,235,100 B2* | 2/2022 | Howard | G16H 40/67 |
| 2009/0194104 A1 | 8/2009 | Van Sickle | |
| 2012/0206605 A1* | 8/2012 | Buehler | G08B 13/19693 348/159 |
| 2016/0210512 A1* | 7/2016 | Madden | G06V 20/52 |
| 2016/0217381 A1 | 7/2016 | Bloomquist et al. | |
| 2018/0092595 A1* | 4/2018 | Chen | A61B 5/1123 |

OTHER PUBLICATIONS

Cai et al., "A cognitive assistive system for monitoring, the use of home medical devices," Proceedings of the 1st ACM Int. workshop on Multimedia indexing and information retrieval for healthcare, 2013, 59-66.
Cote et al., "Evaluation of two different educational interventions for adult patients consulting with an acute astluna exacerbation," American Journal of Respiratory and Critical Care Medicine, 2001, 163(6):1415-9.
Cucchiara et al., "Probabilistic posture classification for human-behavior analysis," IEEE Transactions on Systems, Man and Cybernetics-Part A: Systems and Humans, 2005.
Davis, "Comparison of parametric representations for monosyllabic word recognition in continuously spoken sentences," IEEE Trans. on Acoustics, Speech and Signal Processing, 1980, 28(4):357-366.
Esch et al., "Efficient musical noise suppression for speech enhancement system," In IEEE International Conference on Acoustics, Speech and Signal Processing (ICASSP), Apr. 2009, 4409-4412.
Fathi et al., "Understanding egocentric activities," ICCV, 2011, 1-8.
Fleck et al., "Smart camera based monitoring system and its application to assisted living," Proceedings of the IEEE, 2008, 96(10):1698-1714.

International Preliminary Report on Patentability in International Appln. No. PCT/US2018/064087, dated Jun. 9, 2020, 10 pages.
International Search Report and Written Opinion in International Appln. No. PCT/US2018/064087, dated Feb. 5, 2019, 11 pages.
Iscen et al., "Knives are picked before slices are cut: recognition through activity sequence analysis," In Proceedings of the 5th international workshop on Multimedia for cooking and eating activities, 2013, 6 pages.
Iscen et al., "Snippet histograms for assistive technologies," In ECCV Workshop on Assistive Computer Vision and Robotics (ACVR), 2014, 6 pages.
Kelso et al., "Comprehensive long-term management program for asthma: effect on outcomes in adult African-Americans," The American Journal of the Medical Sciences, 1996, 311(6):272-80.
Kelso et al., "Educational and long-term therapeutic intervention in the ed: effect on outcomes in adult indigent minority asthmatics," American Journal of Emergency Medicine, 1995, 13(6):632-7.
Kitani et al., "Activity forecasting," In ECCV, 2012, 14 pages.
Lee et al., "A robust adaptive generalized sidelobe canceller with decision feedback," IEEE Transactions on Antennas and Propagation, Nov. 2005, 53(11):3822-3832.
Liao et al., "Learning multi-scale block local binary patterns for face recognition," In Advances in Biometrics, 2007, 828-837.
Lu et al., "Story-driven summarization for egocentric video," In CVPR, 2013, 2714-2721.
Martin, "Noise power spectral density estimation based on optimal smoothing and minimum statistics," IEEE Transactions on Speech and Audio Processing, 2001, 9(5):504-512.
McAulay, "Speech enhancement using a soft-decision noise suppression filter," IEEE Transactions on Acoustics, Speech and Signal Processing, 1980, 28(2):137-145.
Mubashir et al., A survey on fall detection: Principles and approaches. Neurocomputing, 2013, 100:144-152.
Patel et al., "Use of metered-dose inhaler electronic monitoring in a real-world asthma randomized controlled trial," The Journal of Allergy and Clinical Immunology: In Practice, 2013, 1(1):83-91.
Pirsiavash et al., "Detecting activities of daily living in first-person camera views," In CVPR, 2012, 2847-2854.
Rodriguez et al., "Analysis of crowded scenes in video," Intelligent Video Surveillance Systems, 2012, 251-272.
Rohrbach et al., "A database for fine grained activity detection of cooking activities," In CVPR, 2012, 1194-1201.
Roshtkhari et al., "Online dominant and anomalous behavior detection in videos," In CVPR, 2013.
Spriggs et al., "Temporal segmentation and activity classification from first-person sensing," In CVPR Workshops, 2009, 8 pages.
Sun et al., "Unsupervised fast anomaly detection in crowds," In ACM MM, 2011, 4 pages.
Tenorth et al., "The turn kitchen data set of evelyday manipulation activities for motion tracking and action recognition," In ICCV Workshops, 2009, 9 pages.
Wang et al., "Action recognition by dense trajectories," In CVPR, 2011, 3169-3176.
Yan et al., "Locally assembled binary (lab) feature with feature-centric cascade for fast and accurate face detection," In CVPR, 2008, 7 pages.
Zhao et al., "Online detection of unusual events in videos via dynamic sparse coding," In CVPR, 2011.
Ziebart et al., "Planning-based prediction for pedestrians," IROS, 2009, 1-6.

* cited by examiner

| No. | Type | Description |
|---|---|---|
| D0 | U | Under no instruction |
| D1 | U | Try to perform as in the turorial |
| D2 | W1 | Forget to shake the inhaler |
| D3 | W2 | Incorrect inhaler position |
| D4 | W3 | Failure to exhale before inhaling |
| D5 | W4 | Failure to hold breath for 10 seconds |
| D6 | W5 | Error sequence |

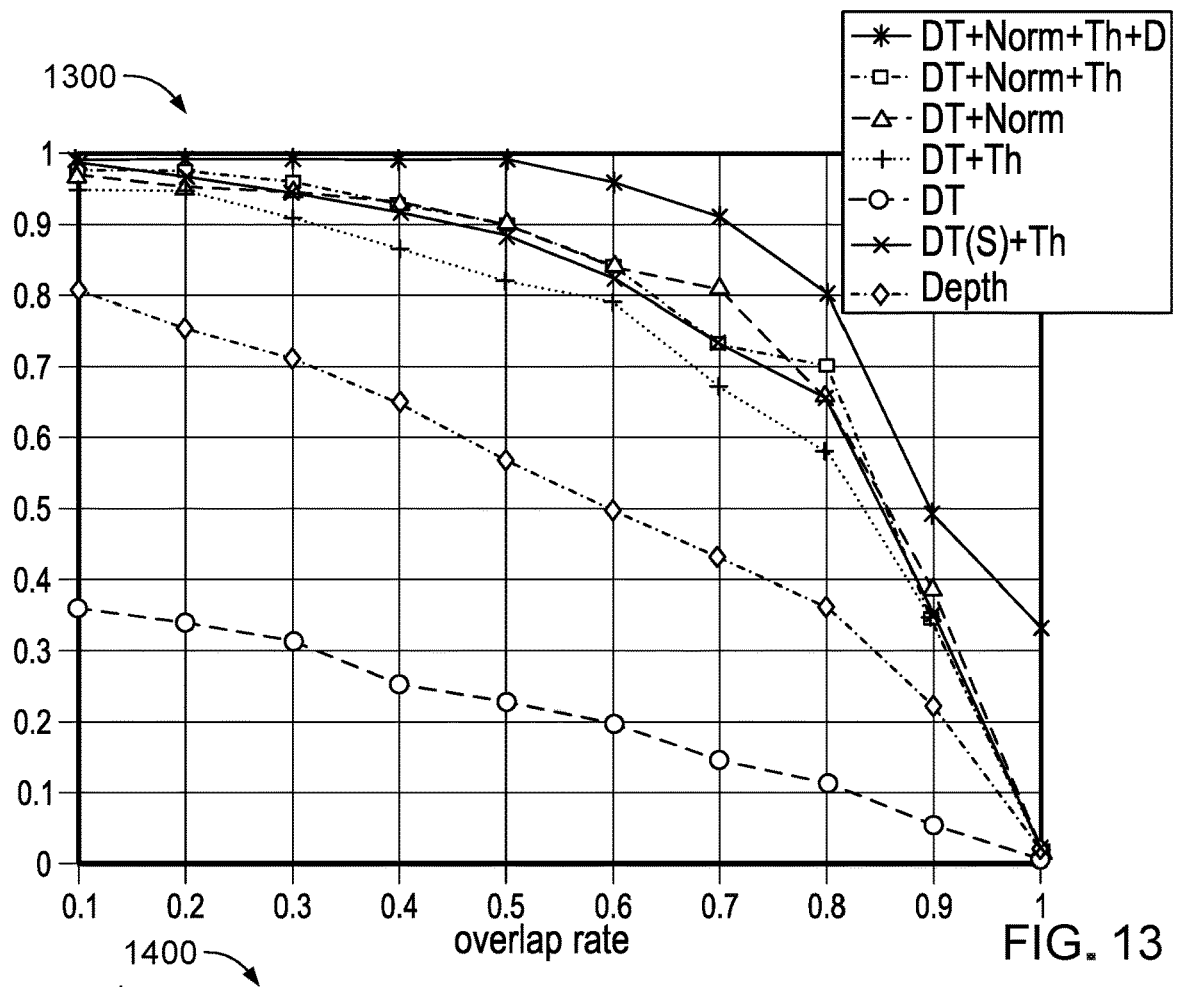
FIG. 13
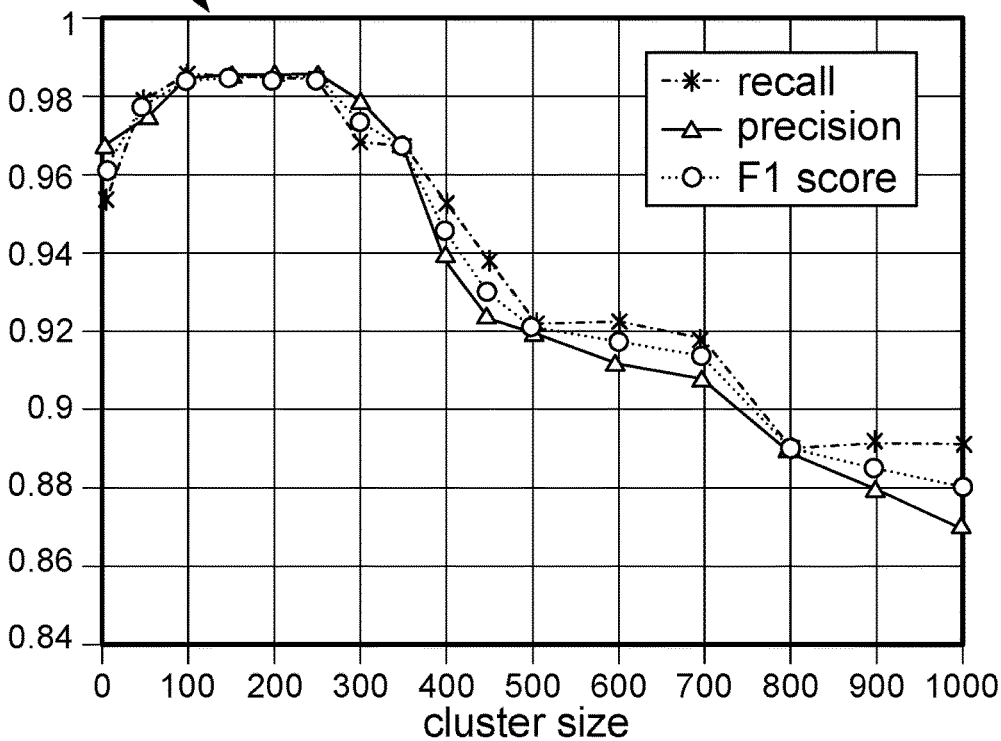
F1 change with number of cluster  FIG. 14A

F1 change with down-sampling rate

DATA PROCESSING SYSTEM FOR CLASSIFYING KEYED DATA REPRESENTING INHALER DEVICE OPERATION

CLAIM OF PRIORITY

This application claims priority under 35 U.S.C. § 119(e) to U.S. Patent Application Ser. No. 62/708,345, filed on Dec. 5, 2017, and claims priority under 35 U.S.C. § 371 to International Application PCT/US2018/064087 filed Dec. 5, 2018 the entire contents of each of which are hereby incorporated by reference.

GOVERNMENT SUPPORT CLAUSE

This invention was made with government support under IIS1251187 awarded by the National Science Foundation. The government has certain rights in the invention.

TECHNICAL FIELD

This document relates to data processing, and more particularly to data classification.

BACKGROUND

Asthma and Chronic Obstructive Pulmonary Disease (COPD) are obstructive airway diseases, mainly distinguishable by the degree of treatability using inhaled beta agonists. Both are chronic diseases with episodic symptom flares, and involve airway inflammation and muscle constriction. Many of the flare-ups or exacerbations result in breathing difficulty severe enough to warrant expensive emergency department visits, hospitalizations, and intensive care stays. Similar medications, such as inhaled corticosteroids and beta agonists, are used to treat both asthma and COPD.

Asthma and COPD are among the among the most common chronic diseases worldwide affecting up to 18% of population. According to the Center for Disease Control, asthma affected about 25.7 million people in the US in 2010 and caused 3,388 deaths in 2009. Despite the recent advances, more than half of asthma patients have poor control and no improvements in asthma outcomes were seen over a recent 10-year span.

Reasons for poor control are numerous and complex, but include the failure to follow asthma guidelines by both physicians and patients. Many physicians are unfamiliar with the asthma guidelines, and even if familiar, do not have sufficient time in an office visit to follow time consuming recommendations for education about trigger avoidance and proper use of medications.

One of the key elements in controlling asthma is good inhaler technique that insures adequate lung delivery to help the underlying airway inflammation. There are several types of inhalers, each with its own set of instructions and steps to follow for administration. The most commonly used inhalers are pressurized metered dose inhalers (pMDI). Standard steps for metered dose inhaler administration have been identified and good technique involves the actuation of the inhaler during a slow (3-5 seconds) deep inhalation using either a closed- or open-mouth technique, followed by 10-second breath hold. However, if the device is used incorrectly, it delivers little or no medication into the lungs, leading to poor clinical outcomes, such as decreased disease control in asthmatics and increased emergency room admissions. Careful management of adherence would help to enhance outcomes, and reduce unnecessary hospitalization and cost. Hence, it is very important for the patients to properly use inhalers for effective disease control.

FIG. 1 illustrates a six-step procedure 100 that should be followed for proper inhaler use. The patient should shake (102) the inhaler first. After exhaling (102), the user (e.g., patient) should hold (104) the inhaler two inches in front of the mouth and exhale (106) before puffing (108). The user should inhale (110) the medicine and hold (112) his/her breath for ten seconds. Finally, he/she should exhale (114) slowly. Although it seems to be a very straightforward procedure, it has been shown that up to 85% of the patients do not use their inhalers correctly. The most common mistakes include failure to exhale before actuation (50%), failure to breath-hold after inhalation (53%), forget to shake before using inhaler (37%) incorrect positioning of the inhaler, and failure to execute a forceful and deep inhalation (52%). Although most of the patients are taught how to use the devices in advance, 25% of them have never received verbal instruction, or the quality and duration of instruction is not adequate and not reinforced by follow-up checks.

Studies have shown that a high proportion of patients do not exhibit adequate inhaler technique, ranging from 58-89%, to enable drug to reach the lungs, thus losing the well-documented preventative effect of inhaled corticosteroids. Even very experienced inhaler users can make important errors in technique. Larsen et al. reported that 77.5%-89.2% of patients with asthma actuated their metered dose inhaler incorrectly. Poor inhaler technique is not confined to metered dose inhalers, however, as patients also make frequent mistakes in the use of dry powder inhalers.

An observational study found that asking children and adolescents to videotape their asthma-management practices at home provided detailed evidence of problems with adherence and inhaler technique. Reviewing these videotape narratives with the patient helped clinicians improve teaching and care of patients; it is shown that the technique improved significantly after metered dose inhaler demonstration, teaching, and reinforcement. However, even patients who initially demonstrate good technique after education can get sloppy in their technique over time, sometimes taking shortcuts or reverting to old habits to make mistakes when using the inhaler. Thus, review of inhaler technique is recommended.

Targeting high-risk patients for asthma education at the emergency department (ED) visit, effect of education on inhaler technique and therefore on the revisits of ED have been explored in two randomized clinical trials (RCTs) and in two observational studies. In a first study, a limited education in the ED in inhaler technique and use of a written asthma action plan was compared to a comprehensive, structured educational program and usual care. ED revisits were not different among the groups in the first 6 months after the intervention, but revisits declined significantly more in the structured education group by 12 months; however, reinforcement of self-management education was provided at the 6-month point only to the structured education group. A second study provided three asthma education sessions to patients after a visit to the ED. Despite significant attrition from attendance at sessions, follow-up was completed with 76 percent of the study sample, and, the intervention group had fewer ED visits at 12-month follow-up.

These studies suggest that new ways involving monitoring and coaching technology to improve inhaler adherence and technique are desperately needed. The data processing system described herein aims to address this need, and results in improvement in asthma control and the reduction of costs associated with asthma.

Recently, assisted living systems have emerged to support elderly or patients who need medical assistance at home. Most of the current systems are based on sensors. This kind of setup is usually very costly and being disruptive not practical for the patient. Most importantly, the captured information is limited.

For inhaler use, electronic monitoring devices that record the date, time, and number of actuation, have also been used to measure medication adherence and patterns of use. However, they share the same drawbacks with the other sensor devices. The alternative is the use of cheap cameras placed in the environment.

SUMMARY

This document describes a data processing system for automated observation, monitoring, and training of patients using metered dose inhalers. The data processing system is configured to coach patients in proper inhaler use by detecting improper usage and providing feedback to the patient. Observations take place using an intelligent data processing system that is interfaced with a camera to identify incorrect actions. Coaching is performed by an interactive system that aims to reinforce good treatment outcomes. The system is based on multimedia analysis techniques utilizing multiple modalities including RGB, depth and audio data collected with a mobile sensing system to discover and bridge the gap between the prescribed steps by doctors and the real daily usages of patients. A rule-based joint classification method then provides personalized feedback to coach patients, in real time, to improve their performance. Embodiments of the present invention include, but are not limited to data input from a camera-based system (e.g. a Kinect), audio and infrared (IR) data.

The data processing system described herein provides the following advantages. The data processing system is able to guide patients to use inhalers correctly, and includes a fast responding detection system that is able to warn the patient when incorrect usage occurs. The data processing system can be passive and use low-cost cameras to obtain the information that is required to classify inhaler operations. The classification of the inhaler operations is improved by using depth and audio information and are combined with a rule based coaching system. In this way, no specialized inhaler is required, but rather any inhaler device operation can be monitored and classified by the data processing system. The system can be passive when monitoring and interactive when coaching to enable users to operate the inhaler normally (e.g., as if the data processing system were not present) and receive feedback regarding inhaler operation. For example, when a particular step of inhaler operation is incorrect, out of order, omitted, etc., the data processing system can provide this feedback to the patient to perform corrective action.

The data processing techniques described herein enable classification of inhaler operations with increased accuracy relative to the classification accuracy of conventional systems. Additionally, the data processing techniques described herein enable fast (e.g., real-time) classification of inhaler operations so that a user can be coached in inhaler operation while using the inhaler. To accomplish this, the data processing system includes parallel classification systems that each monitor for difference inhaler actions simultaneously. This enables the data processing system to determine if operations are occurring out of sequence while the user is operating the inhaler, as opposed to receiving a video clip after the completion of the operations for post-processing.

Additionally, an automatic system is cost saving because a particular inhaler device need not be purchased, but rather any inhaler device can be used with the data processing system. The data processing system is convenient as patients decide when and where to use the system for learning and reinforces the proper procedures of inhaler usage.

A data processing system for digitally processing live data feeds of inhaler device operation includes in-memory data storage configured to obtain, from one or more external data sources, a live data feed representing operation of an inhaler device. The in-memory data storage is configured to index the live data feed with a key value representing the inhaler device for which the live data feed is obtained. The data processing system includes a digital processing engine configured to, for a particular key value indexed in the in-memory data storage, query, from the in-memory data storage, a live data feed representing physical operation of an inhaler device, with the live data feed being indexed to that particular key value, segment the live data feed for that particular key value into a plurality of data samples, digitally process at least a portion of the data samples to classify each of the processed data samples, and based on the classified data samples, output a prompt specifying whether operation of the inhaler device is within a threshold range of operation.

In some implementations, the data processing system includes a shake classification engine configured to receive video data. In some implementations, the shake classification engine, for each frame of the video data, samples a portion of the frame, the portion of the frame corresponding to a position of an inhaler in the frame, determines, responsive to sampling the portion of each frame, a distance value representing a change in position of the portion between each frame of the video data, generates a vector comprising the distance value and additional distance values determined for additional portions of each frame of the video data, the additional portions corresponding to a representation of a user in each frame, applies a video classifier to the vector, the video classifier being trained with training data indicative of correct shaking of the inhaler, and responsive to applying the video classifier, outputs shake classification data indicative of a likelihood that the video data is indicative of the correct shaking of the inhaler.

In some implementations, the data processing system includes a position classification engine configured to receive the video data. For each frame of the video data, the position classification engine performs operations including segmenting the frame into a plurality of subsections, applying, to at least one subsection of the plurality of subsections, a plurality of binary classifiers, the plurality of binary classifiers indicating that the at least one subsection comprises a representation of a first anatomical feature face of the user or a second anatomical feature, retrieving a first range value associated with a first subsection comprising a representation of the first anatomical feature of the user in the frame, retrieving a second range value associated with a second subsection comprising a representation of the second anatomical feature of the user in the frame, determining that a difference between the first range value and the second range value is less than a threshold difference, and outputting position data indicating a likelihood that the inhaler is correctly positioned relative to the user.

In some implementations, the data processing system includes an audio classification engine configured to receive audio data corresponding to the video data, encode the audio data into a power spectrum, estimate a noise component of the power spectrum, filter the noise component from the power spectrum to generate a filtered power spectrum, apply an audio classifier to the filtered power spectrum, the audio classifier being trained with training data indicative of one or more of an exhalation sound, an inhalation sound, and an inhaler puff sound; and responsive to applying the audio classifier, output audio classification data indicative of a likelihood that the audio data is indicative of the exhalation sound and a likelihood that the audio data is indicative of the inhaler puff sound.

In some implementations, the data processing system includes a rule logic engine configured to receive the audio classification data, the shake classification data, and the position data, based on the audio classification data, the shake classification data, and the position data, determine that the video data and the audio data represent a shake event, a position event, a puff event, and an exhalation event, determine an order for the shake event, the position event, the puff event, and the exhalation event, and responsive to determine that the order matches a predefined order of events, output data representing instructions for inhaler operation by the user.

In some implementations, the video classifier and the audio classifier each comprises a support vector machine.

In some implementations, the distance value represents a trajectory value that is calculated using a dense trajectory feature.

In some implementations, the shake classification engine, the position classification engine, and the audio classification engine operate in parallel and in real-time as the as the live data feed is obtained.

In some implementations, the data processing system further includes a camera for obtaining video data, a microphone for obtaining audio data, and a ranging sensor for obtaining first and second range values.

In some implementations, the plurality of binary classifiers are a portion of a locally assembled binary (LAB) cascade face detector. In some implementations, the power spectrum comprises a mel-frequency cepstrum.

In some implementations, the rule logic engine is further configured to determine that a time between the puff event and an additional exhalation event exceeds ten second, and responsive to determining that the time exceeds ten seconds, output data indicating correct usage of the inhaler by the user.

In some implementations, the data processing system further includes a user interface configured to display the data representing instructions for inhaler operation by the user, the data comprising a status indicator for one or more of the shake event, the position event, the puff event, and the exhalation event, the status indicator for each respective event representing a pass or fail for the respective event. In some implementations, the user interface is configured to display one or more instructions indicative of corrective action in response to a determination by the rule logic engine that the order does not match the predefined order of events or that one or more of the shake event, the position event, the puff event, and the exhalation event are not represented by the audio data and the video data.

In some implementations, the data processing system further includes a temperature sensor for obtaining temperature data.

In some implementations, a method for classification of data representing a plurality of inhaler operations, includes obtaining, by an in-memory data storage from one or more external data sources, a live data feed representing operation of an inhaler device, indexing, by the in-memory data storage, the live data feed with a key value representing the inhaler device for which the live data feed is obtained, and for a particular key value indexed in the in-memory data storage: querying, by a digital processing engine, from the in-memory data storage, a live data feed representing physical operation of an inhaler device, with the live data feed being indexed to that particular key value, segmenting, by the digital processing engine, the live data feed for that particular key value into a plurality of data samples, processing, by the digital processing engine, at least a portion of the data samples to classify each of the processed data samples, and based on the classified data samples, outputting a prompt specifying whether operation of the inhaler device is within a threshold range of operation.

In some implementations, the method further includes receiving video data, for each frame of the video data: sampling a portion of the frame, the portion of the frame corresponding to a position of an inhaler in the frame, determining, responsive to sampling the portion of each frame, a distance value representing a change in position of the portion between each frame of the video data, and generating a vector comprising the distance value and additional distance values determined for additional portions of each frame of the video data, the additional portions corresponding to a representation of a user in each frame. In some implementations, the method further includes applying a video classifier to the vector, the video classifier being trained with training data indicative of correct shaking of the inhaler, and responsive to applying the video classifier, outputting shake classification data indicating a likelihood that the video data is indicating the correct shaking of the inhaler.

In some implementations, the method further includes, for each frame of the video data, segmenting the frame into a plurality of subsections, applying, to at least one subsection of the plurality of subsections, a plurality of binary classifiers, the plurality of binary classifiers indicating that the at least one subsection comprises a representation of a first anatomical feature face of the user or a second anatomical feature, retrieving a first range value associated with a first subsection comprising a representation of the first anatomical feature of the user in the frame, retrieving a second range value associated with a second subsection comprising a representation of the second anatomical feature of the user in the frame, determining that a difference between the first range value and the second range value is less than a threshold difference; and, outputting position data indicating a likelihood that the inhaler is correctly positioned relative to the user.

In some implementations, the method further includes receiving audio data corresponding to the video data, encoding the audio data into a power spectrum, estimating a noise component of the power spectrum, filtering the noise component from the power spectrum to generate a filtered power spectrum, applying an audio classifier to the filtered power spectrum, the audio classifier being trained with training data indicative of one or more of an exhalation sound, an inhalation sound, and an inhaler puff sound, and responsive to applying the audio classifier, outputting audio classification data indicative of a likelihood that the audio data is indicative of the exhalation sound and a likelihood that the audio data is indicative of the inhaler puff sound.

In some implementations, the method further includes receiving the audio classification data, the shake classification data, and the position data, based on the audio classification data, the shake classification data, and the position data, determining that the video data and the audio data represent a shake event, a position event, a puff event, and an exhalation event, determining an order for the shake event, the position event, the puff event, and the exhalation event, and responsive to determining that the order matches a predefined order of events, outputting data representing instructions for inhaler operation by the user.

In some implementations, the video classifier and the audio classifier each comprises a support vector machine. In some implementations, the distance value represents a trajectory value that is calculated using a dense trajectory feature. In some implementations, the method includes operating a shake classification engine, a position classification engine, and an audio classification engine in parallel and in real-time as the live data feed is obtained.

In some implementations, further includes operating a camera for obtaining video data, a microphone for obtaining audio data, and a ranging sensor for obtaining first and second range values.

In some implementations, the plurality of binary classifiers are a portion of a locally assembled binary (LAB) cascade face detector.

In some implementations, the power spectrum comprises a mel-frequency cepstrum.

In some implementations, the method includes determining that a time between the puff event and an additional exhalation event exceeds ten seconds, and responsive to determining that the time exceeds ten seconds, outputting data indicating correct usage of the inhaler by the user.

In some implementations, the method further includes displaying, by a user interface, the data representing instructions for inhaler operation by the user, the data comprising a status indicator for one or more of the shake event, the position event, the puff event, and the exhalation event, the status indicator for each respective event representing a pass or fail for the respective event.

In some implementations, the method further including displaying, by a user interface, one or more instructions indicative of corrective action in response to a determination by the rule logic engine that the order does not match the predefined order of events or that one or more of the shake event, the position event, the puff event, and the exhalation event are not represented by the audio data and the video data.

In some implementations, the method includes obtaining temperature data from a temperature sensor.

In some implementations, the data processing system is configured for parallel classification of data representing a plurality of inhaler operations. In some implementations, the data processing system includes a shake classification engine configured to classify image data, wherein the image data comprises a series of images representing a shaking operation of an inhaler. In some implementations, the shake classification engine is configured to receive the image data comprising the series of images, perform a thresholding operation on an initial image of the series of images to identify one or more features in the initial image, sample the initial image at the one or more features to obtain a plurality of feature points, each feature point comprising data indicating a location of that feature point in the initial image, for each feature point of the plurality, generate a trajectory vector by: determining a location of the feature point in a next image in the series of images, determining a displacement value between the location in the initial image of the feature point and the location of the feature point in the next image, adding the displacement value to a total displacement value representing the trajectory vector, and replacing the initial image with the next image. In some implementations, the displacement value is determined for each subsequent image in the series of images and added to the total displacement value. In some implementations, the shake classification engine generates a code vector representing the generated trajectory vectors, the code vector configured for inputting into support vector machine logic of the shake classification engine, and outputs, by the support vector machine logic, a classification of the code vector, the classification indicative of a likelihood that the shaking operation of the inhaler is correct.

In some implementations, the data processing system further comprises a position classification engine configured to further classify the image data, and the image data comprises images representing a position of a face of a user relative to the inhaler. In some implementations, the position classification engine is configured to receive the image data comprising the series of images, and for each image: segment the image into a plurality of subsections; apply, to at least one subsection of the plurality of subsections, a plurality of binary classifiers to generate a classification vector for the at least one subsection, the classification vector indicating which binary classifiers are satisfied, and the plurality of binary classifiers indicating that the face of the user or the inhaler is present in the at least one subsection, compare the classification vector to a threshold vector, wherein the subsection of the image includes the face of the user or the inhaler when values the classification vector satisfies the threshold vector, retrieve a first range value associated with a first subsection comprising the face of the user in the image, retrieve a second range value associated with a second subsection comprising the inhaler in the image, and output position data indicating that the position of the face of the user relative to the inhaler is correct when a difference between the first range value and the second range value is less than a predefined threshold difference.

In some implementations, the data processing system further includes an audio classification engine configured to classify audio data. The audio classification engine is configured to receive the audio data, encode the audio data into a short-term power spectrum, estimate a noise component of the short-term power spectrum, filter the noise component from the short-term power spectrum to generate a filtered short-term power spectrum, apply support vector machine logic to the filtered short-term power spectrum, and output a classification of the short-term power spectrum, the classification indicative of a likelihood that the audio data represents an inhalation sound of the user or a likelihood that the audio data represents a puff activation of the inhaler.

In some implementations, the data processing system includes a rules logic engine configured to receive the classification of the code vector, the position data, and the classification of the short-term power spectrum, apply a threshold to the classification of the code vector, the position data, and the classification of the short-term power spectrum, determine, responsive to applying the threshold, that each of a shaking event, a puff event, a position event, and an exhaling event are represented in the image data and the audio data, determine that an order of the shaking event, the puff event, the position event, and the exhaling event matches a predefined order, and in response determining that the order matches the predefined order, output data indicating that the user is correctly using the inhaler.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 12-19 show test results data from testing the data processing system.

DETAILED DESCRIPTION

A data processing system is configured to classify keyed data representing inhaler device operation to provide feedback to a user regarding inhaler operation by the user. The feedback is generated as the user is using the inhaler device. A user interface updates to inform the user that the inhaler is being used properly, or that an error has occurred. Classification engines of the data processing system can operate in parallel to ensure that events are detected as they occur and in real-time or near real time. The near-instantaneous feedback of the data processing system improves medical outcomes of inhaler device operation. The data processing system provides data to users as they are using the inhaler device to inform the user exactly how to operate the inhaler device correctly. The data processing system can interactively coach the user to operate the inhaler device correctly, which improves medicine delivery to the user from the inhaler and thus the medical effectiveness of inhaler operation for that user. Furthermore, the data processing system keys data feeds to the user, so that the user can have a profile that can be provided to medical care providers. The keyed data can be used by the medical care providers to change inhaler design and further improve medical outputs for patients.

Figure 2A:
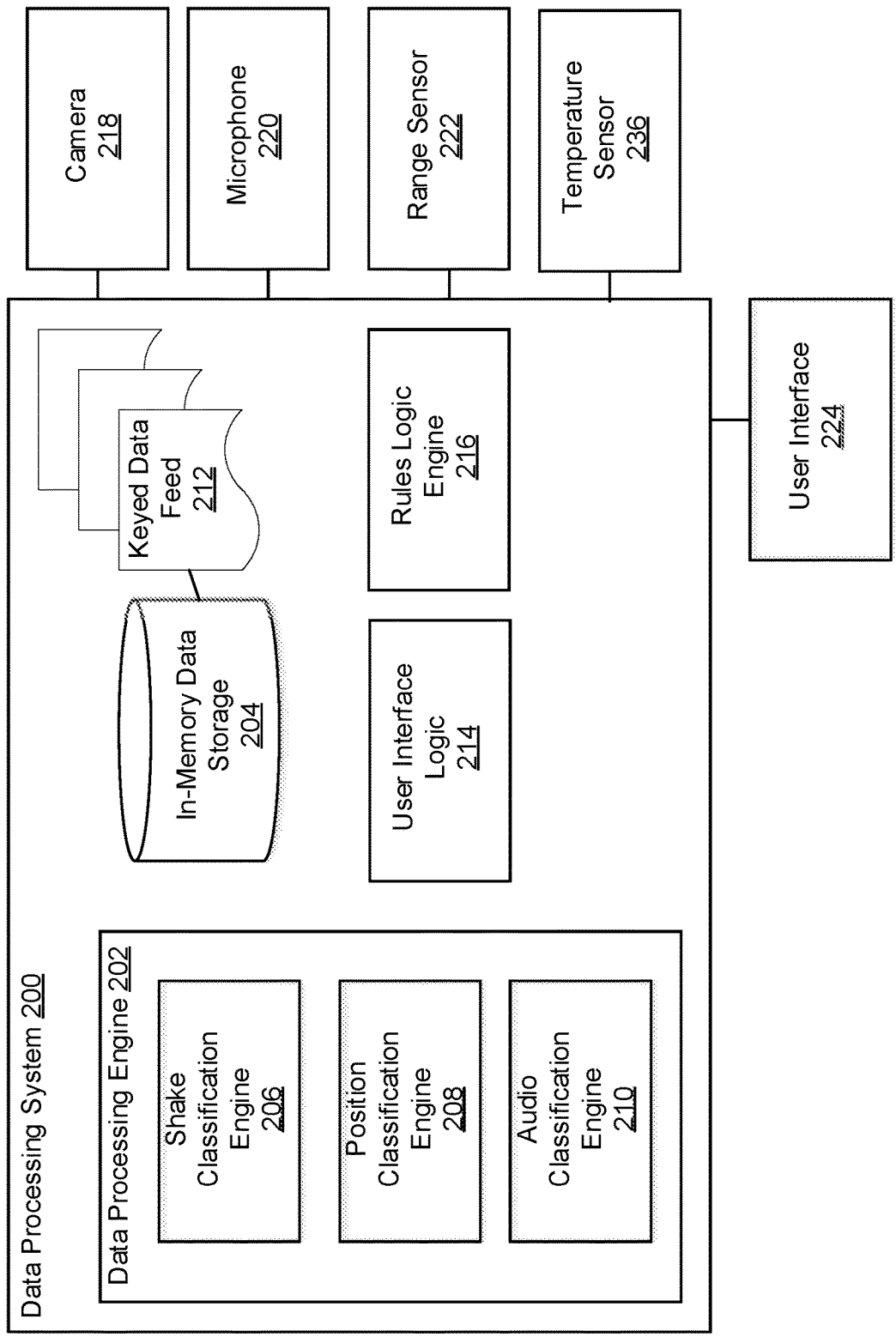
FIG. 2A shows an example data processing system for classifying keyed data representing inhaler device operation.

FIG. 2A shows an example data processing system 200 for digitally processing live data feeds of the inhaler device operation. The data processing system 200 includes a digital processing engine 202 and an in memory data storage 204. The data processing engine 202 includes a plurality of classification engines 206, 208, 210 each configured to execute logic for classification of the live feed representing the inhaler operations. The plurality of classification engines include a shake classification engine 206, a position classification engine 208, and an audio classification engine 210. Each of these classification engines is described in further detail below. The data processing system 200 further includes user interface logic 214 for generating visualizations of live data feeds received by the data processing system 200 and generating feedback to a user of an inhaler device related to the operation of the inhaler device by the user. The data processing system 200 includes a rules logic engine 216 configured to make determinations, once the classification engines 206, 208, 210 have classified the live data feed, whether the inhaler operation is correct or whether inhaler operation is incorrect. In some implementations, the data feeds need not be live data feeds. The data processing system 200 can be used with previously recorded data feeds, to determine if previous inhaler operation was correct.

In some implementations, the data processing system 200 can communicate with one or more sensors for capturing the live data feeds, such as a camera 218 to capture video data 230, a microphone 220 to capture audio data 234, a range sensor 222 to capture range data 232 indicating a distance of objects from the camera 218, and a temperature sensor 236 for capturing thermal data 238 (e.g., temperature data). In some implementations, the data processing system 200 includes the one or more sensors 218, 220, 222, 236.

Figure 2B:
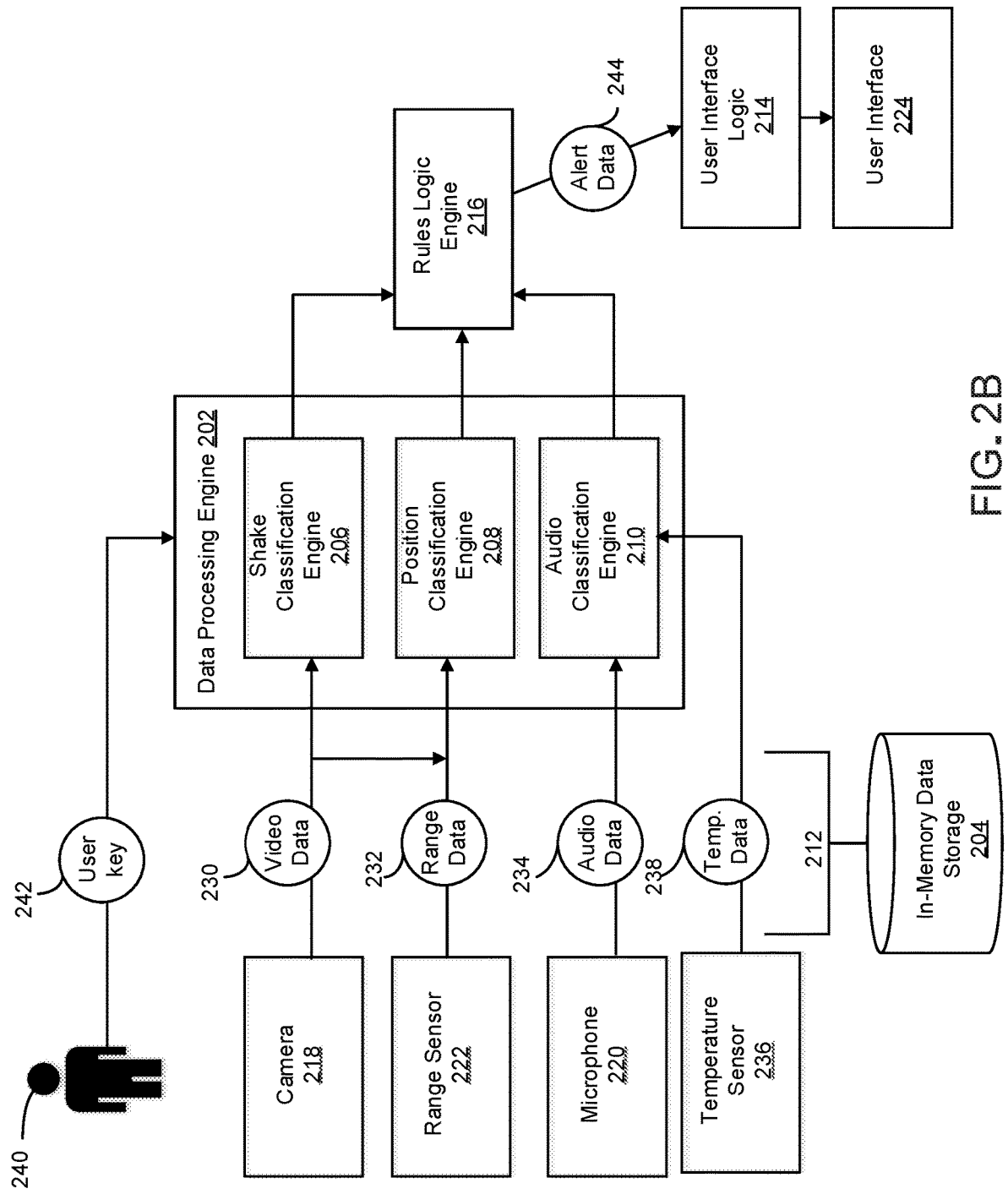
FIG. 2B shows an example data flow for the data processing system of FIG. 2A.

The data processing system 200 classifies keyed data 212 representing the inhaler operation as shown by the dataflow diagram in FIG. 2B. A user 240 (e.g., a patient) stands in view of the one or more sensors so that a live data feed 212 can be captured of the user operating the inhaler device. The user 240 is associated with a user key 242. The user key 242 can be assigned to the data feed 212 that includes a representation of that user 240 for any data feed that represents that user. The key 242 thus acts as an identifier to identify the particular user 204 among many users represented by data feeds stored in the in-memory data storage 204. The live data feed 212 is thus stored as a keyed data feed that is keyed with key 242 to the user 240.

One or more sensors capture the data feed 212 data for classification by the data processing system 200. The camera 218 captures video data 230 of the inhaler operation by the user 240. In some implementations, the camera 218 sends the video data 230 to the shake classification engine 206 and the position classification engine 208 of the data processing engine 202. The range sensor 222 captures range data 232. The range data 232 represents, for example, how far each pixel (or groups of pixels of the video data 230) are from the camera 218 in physical space. In some implementations, the range sensor 222 is independent of the camera 218 and provides range data indicative of a distance of the user 240 from the range sensor 222. The range data 232 can be calibrated to represent a distance of the user 240 (or any object in the video data 230) from the camera 218. The range data 232 is sent to the position classification engine 208 of the data processing engine 202. The microphone 220 captures audio data 234. The audio data 234 includes any sounds made by the user 240, the inhaler device, or other objects in the environment of the user 240. The audio data 234 is sent to the audio classification engine 210 of the data processing engine 202. The temperature sensor 236 captures temperature data 238. The temperature data 238 includes temperature measurements and/or temperature gradients in the environment around the user 240. Specifically, the temperature sensor 236 measures temperatures near a mouth of the user 240 to assist determination of whether the user 240 is inhaling or exhaling. In some implementations, the video data 230, range data 232, audio data 234, and temperature data 238 are synched to a global time so that, during classification, the relative temporal occurrences of one or more events that are classified by the data processing engine 202 can be compared in time with one another to ensure that a correct sequence of operations occurred, and to classify the events themselves. The video data 230, the range data 232, and the audio data 234 comprise the live data feed 212 that is classified by the data processing engine 202. In some implementations, the live data feed 212 can be stored in the in-memory data storage 204 along with the key 242 that identifies the user 240, thereby associating the user 240 with the data feed 212 in the in-memory data storage 204.

The data processing engine 202 receives the live data feed 212 and classifies data of the live data feed to determine whether inhaler operations occurred, and the order of the inhaler operations that occurred. Each of the operations of the shake classification engine 206, the position classification engine 208, and the audio classification engine 210 is described in detail below. Once the live data feed 212 has been classified into inhaler operation events, the classification engines 206, 208, 210 each output likelihoods that the events occurred.

Figure 1:
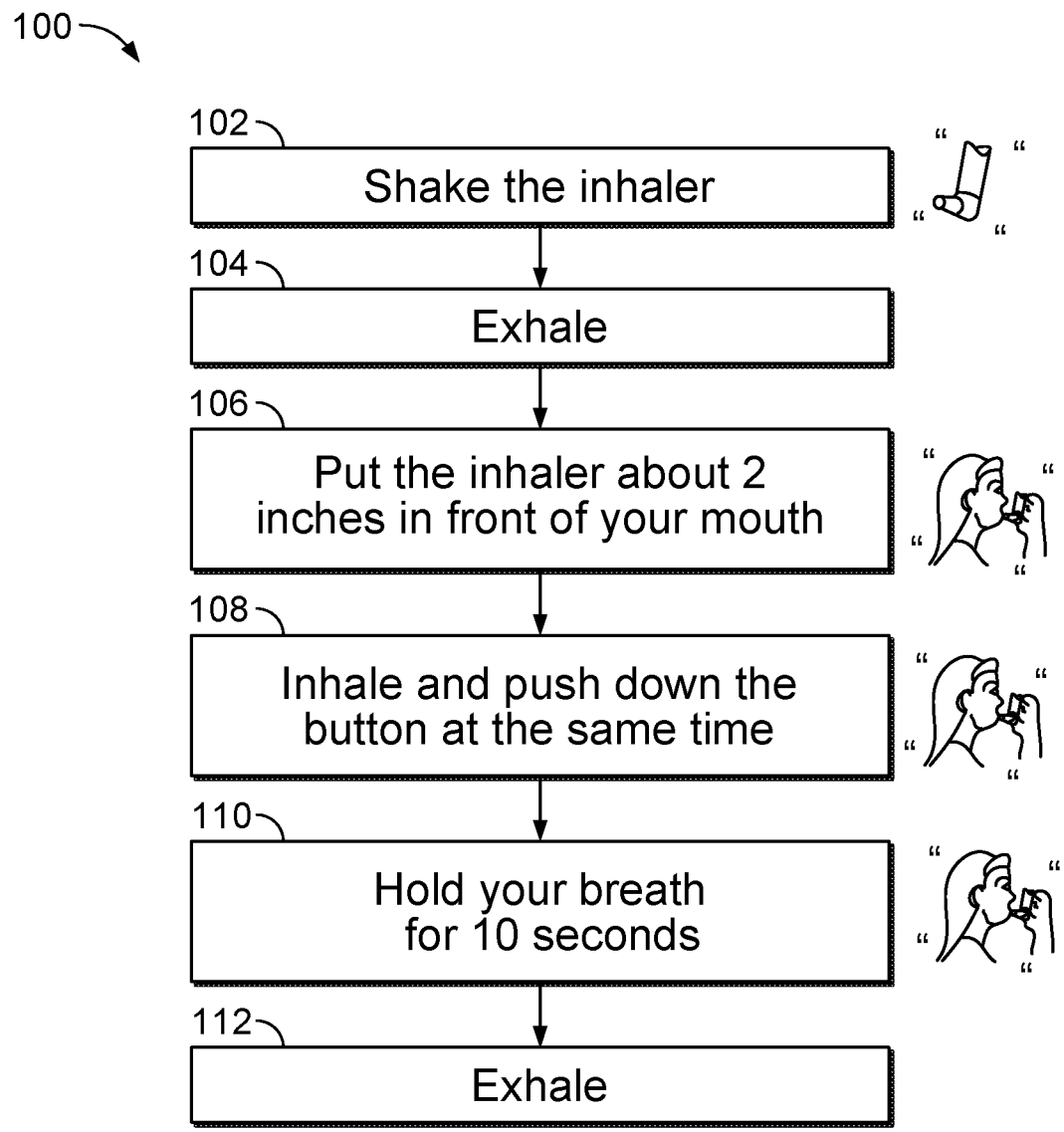
FIG. 1 shows a flow diagram of the correct procedure of using an inhaler.

The rules logic engine 216 receives the classification outputs (e.g., percent likelihoods) and determines whether proper operation of the inhaler device occurred. For example, the rules logic engine 216 can check for one or more missing events, events occurring out of sequence from a predefined sequence (e.g., the sequence 100 of FIG. 1). If one or more errors are found, the rules logic engine 216 can generate alert data 244 for informing the user 240 that the inhaler device has been improperly used. The alert can include, for example, which event of sequence 100 was omitted, which event was out of sequence, how the event was failed (e.g., the delay was not long enough, the inhaler position was too far away, the inhaler was not shaken for long enough, etc.). In some implementations, if the inhaler is used correctly, the alert data 244 includes an indication that the inhaler was used properly.

The alert data 244 is sent to a user interface logic 214 which generates a visual display for a computing device (not shown) hosting the data processing system 200. The user interface 224 of the host computing system generates the visual display to coach the user 240 as the user operates the inhaler device.

In some implementations, the alert data 244 is generated in real-time as the user is using the inhaler device. The user interface updates to inform the user that the inhaler is being used properly, or that an error has occurred. For example, the user interface may include a timer to countdown a delay between a detected exhalation sound and a puff sound. The classification engines 206, 208, 210 can operate in parallel to ensure that events are detected as they occur and in real-time or near real time. The near-instantaneous feedback of the data processing system 200 improves medical outcomes of inhaler device operation because it provides data to users as they are using the inhaler device to inform the user exactly how to operate the inhaler device correctly. The data processing system 200 can interactively coach the user 240 to operate the inhaler device correctly, which improves medicine delivery to the user 240 from the inhaler.

Figure 2C:
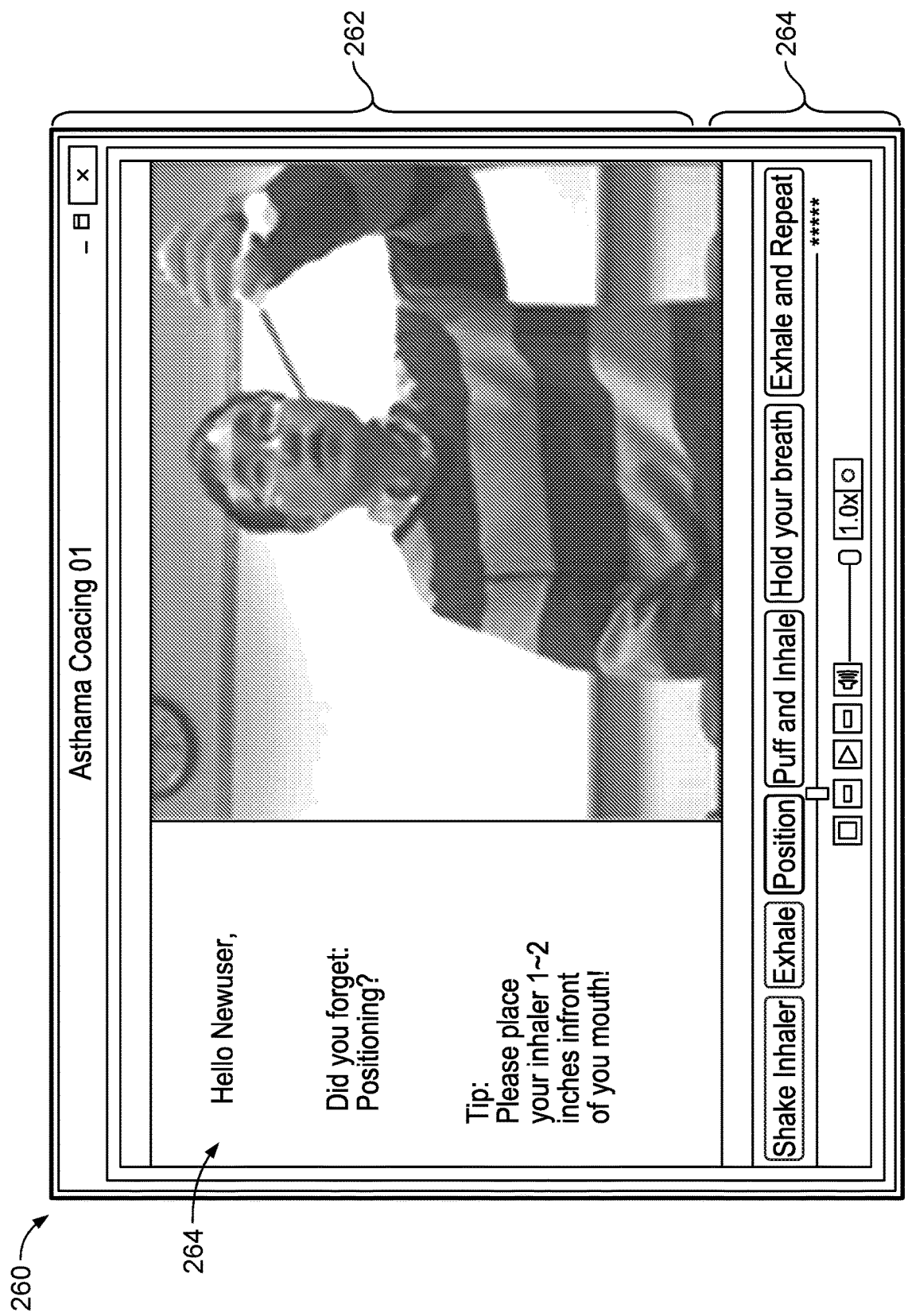
FIG. 2C shows an example user interface for the data processing system of FIG. 2A.

FIG. 2C shows an example user interface 260. The user interface 260 shows a representation 262 of the live video feed captured by the one or more sensors as described above. The user interface 260 includes one or more controls 264, such as for selecting an event to coach/monitor of sequence 100 and to display the current event in the sequence to be performed. The user interface 260 includes an alert pane 264 for displaying alerts, instructions, and other feedback for inhaler operation.

Figure 3:
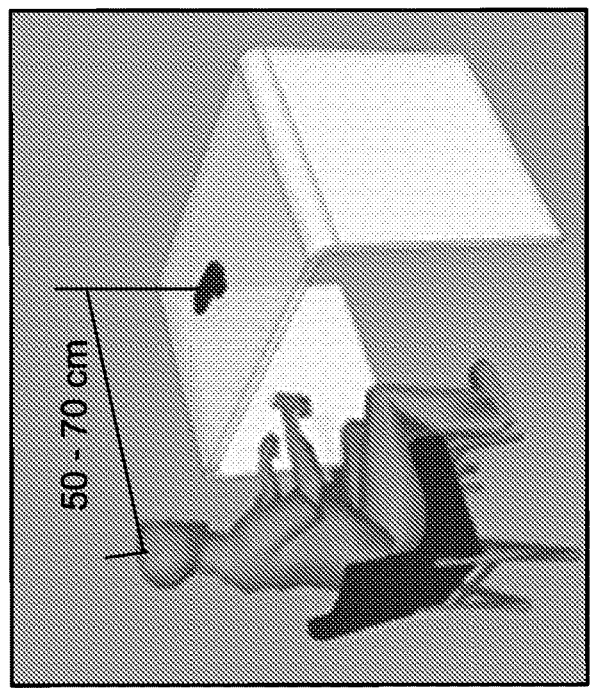
FIG. 3 shows an example environment for using the data processing system 200.

For verifying operation of the data processing system 200, a dataset for studying the use of inhaler was collected. An example of inhaler was a GlaxoSmithKline Inhalation Aerosol. As FIG. 3 shows, a Kinect can be used to record RGB, depth and audio data. However, any sensing system may be used to capture the live data feed 212 as described above. In the example setup 300 shown in FIG. 3, the user sits about 50 to 70 cm away from the Kinect while using the inhaler device.

For this experiment, recordings were obtained from 11 volunteers. Each subject performed 7 times, each time simulating a possible condition 302. The first set (D0) was recorded under no instructions. Rather, the subjects performed based on their own experience. The result type is unknown (U), which can be either correct (C) or wrong (W). The subjects watched a tutorial video and performed again. Common mistakes encountered in real patients were simulated by asking the subjects to intentionally make one action improperly (W1-W5) in the following five recordings (D2-D6). In total, there were 77 videos.

After consulting doctors and following the manual of the inhaler, the original recordings were manually labeled for four events (shaking, positioning, puffing and exhaling) as time sequences. In addition, whether the patient requires improvement was also examined and labeled accordingly based on the observed improper inhaler techniques (W1-W5).

There are five main actions in the sequence of correct inhaler usage. The actions include inhaler shaking, inhaler positioning, inhaling, exhaling and triggering a puff of aerosol. To analyze patients' behavior, a multi-modal approach is used. The multi-modal approach exploits information from RGB and depth cameras together with audio data, as described above.

The first step before using the inhaler is to shake it to distribute the medication properly. With the fact that every patient has his/her own style in shaking (one might shake the hand slightly, while others may shake the entire arm vigorously, one performs vertical shaking while another does horizontal shaking at different position), a robust and applicable approach is crucial for detecting inhaler shaking. The common properties observed for inhaler shaking are periodical and fast motion. These properties suggest the use of a feature that encodes trajectories of local motions and thus we exploit the state-of-the-art dense trajectory feature for this purpose.

As in the original dense trajectory extraction method, points are densely sampled in a grid on different spatial scales, and these points are tracked for L frames using optical flow. $T=\{(x_1, x_1) \ldots (x_L, x_L)\}$ is the resulting L trajectory points. Then, mean of x and y values are calculated, and subtracted from each point. Then, static trajectories with very low variances and random trajectories with very high variances are removed. To normalize the points the length of the trajectory, i.e.

$$\text{Length}(T) = \Sigma_{i=1}^{L} \sqrt{(x_{i+1}-x_i)^2 + (y_{i+1}-y_i)^2} \text{ is computed.}$$

Finally, normalized trajectory points are used to have a 2 L dimensional feature vector. Because shaking is a fast motion that generates many long trajectories, a threshold $\theta_t$ is applied on the length of trajectories to eliminate noisy short trajectories caused by irrelevant random body movements. The dense trajectory extraction method used is further described in H. Wang, A. Klaser, C. Schmid, and C.-L. Liu. Action recognition by dense trajectories. In CVPR, pages 3169-3176, 2011, incorporated herein in entirety by reference.

Figure 4:
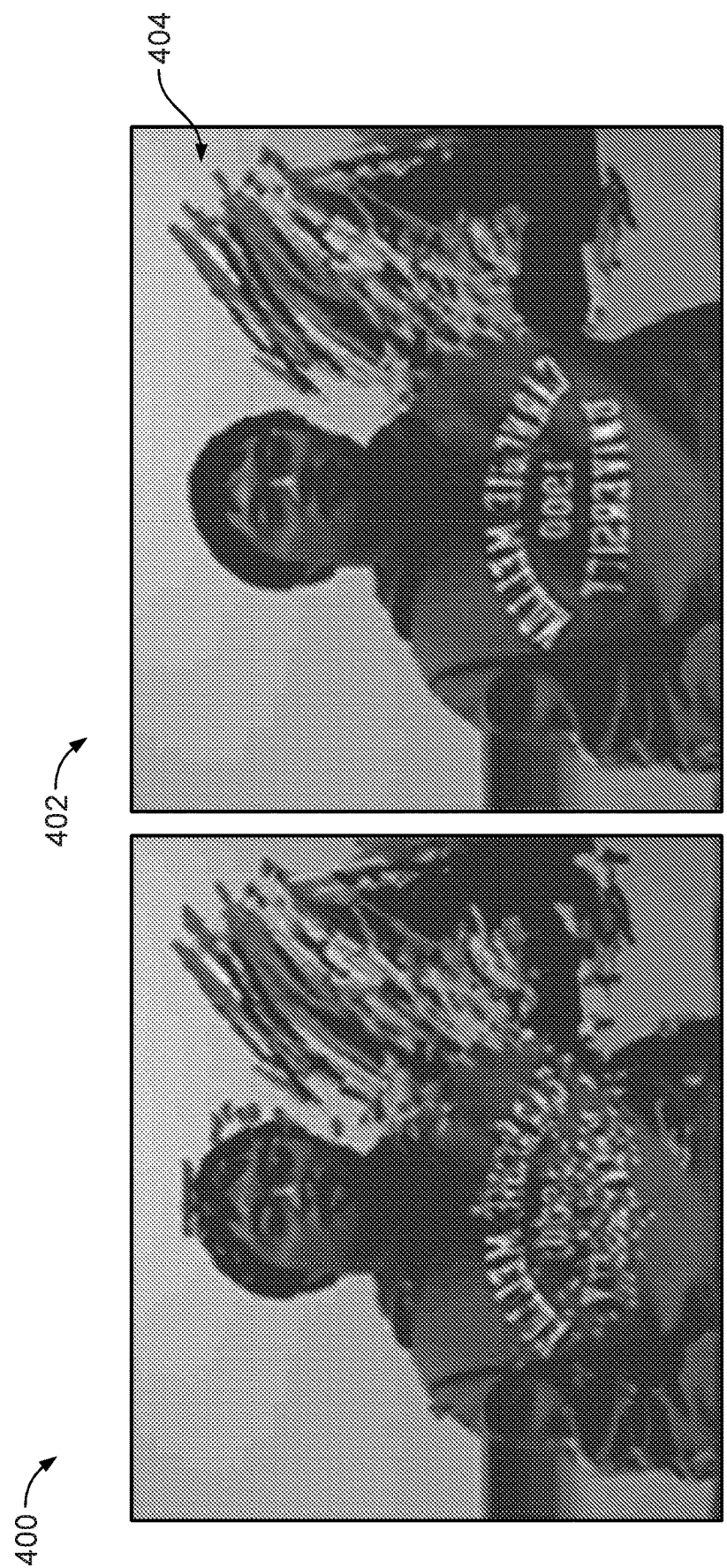
FIG. 4 shows dense trajectories before and after a threshold is applied.

FIG. 4 shows example images 400, 402 including calculated trajectories 404 that remained after setting trajectory length threshold $\theta_t$ to 100 pixels.

As a further improvement, the background is removed and extract the trajectories only on the foreground. For background detection, the depth information is used, and simple method is used for thresholding based on applying a threshold $\theta_d$ to the depth values.

The videos are divided into short clips with length w frames. Bag-of-Words representation is used to describe each clip. A codebook with K words is constructed and each trajectory is assigned to the closest visual word according to Euclidean distance. Support Vector Machine (SVM) was used to train a binary shaking classifier. The output of SVM is then being smoothed by an alpha filter with smoothing factor $\alpha_s$.

Figure 5:
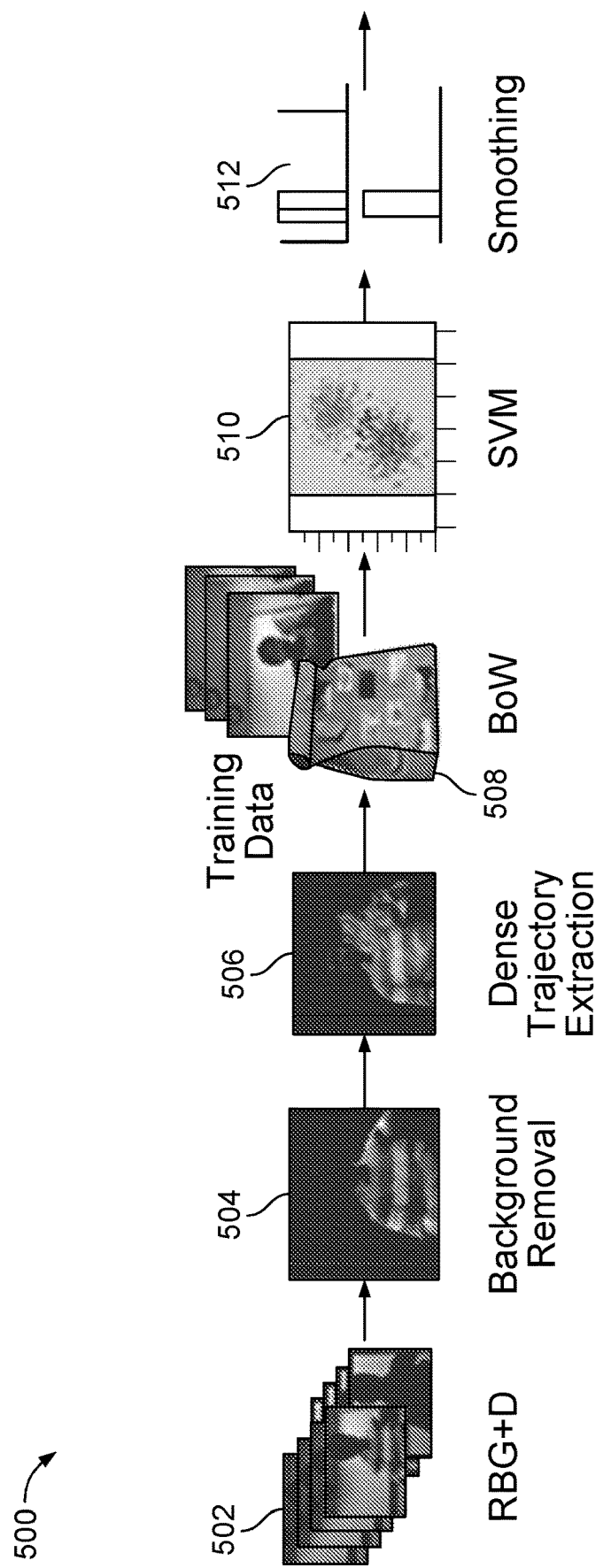
FIG. 5 shows an example pipeline for shaking classification.

The pipeline 500 for shaking detection is shown in FIG. 5. Note that, for real-time coaching, the data processing system 200 features low-delay detection. Therefore, the time-consuming HOG, HOF and MBH based descriptors are not used, but rather only the shape of the trajectories are used. This reduces processing time of the shake classification.

The pipeline 500 of FIG. 5 can be further described as follows. The shake classification engine 206 receives (502) the image data comprising a series of images. The shake classification engine 206 performs background removal (504) on the series of images. For example, the shake classification engine executes a thresholding operation on an initial image of the series of images to identify one or more features in the initial image. The shake classification engine 206 samples (506) the initial image at the one or more features to obtain a plurality of feature points, each feature point comprising data indicating a location of that feature point in the initial image. For each feature point of the plurality, the shake classification engine 206 generates a trajectory vector by determining a location of the feature point in a next image in the series of images, determining a displacement value between the location in the initial image of the feature point and the location of the feature point in the next image, adding the displacement value to a total displacement value representing the trajectory vector; and replacing the initial image with the next image, where the displacement value is determined for each subsequent image in the series of images and added to the total displacement value. The shake classification engine 206 generates (508) a code vector representing the generated trajectory vectors, the code vector configured for inputting into support vector machine logic of the shake classification engine. The shake classification engine 206 outputs (510), by the support vector machine logic, a classification of the code vector, the classification indicative of a likelihood that the shaking operation of the inhaler is correct. In some implementations, a final smoothing (512) operation occurs.

Turning to position checking, before triggering a puff of aerosol of the inhaler, a patient must place the inhaler at around two (2) inches away from his/her mouth. To detect the distance between the asthma inhaler and the user's mouth, depth information provided by Kinect was utilized.

Figure 6:
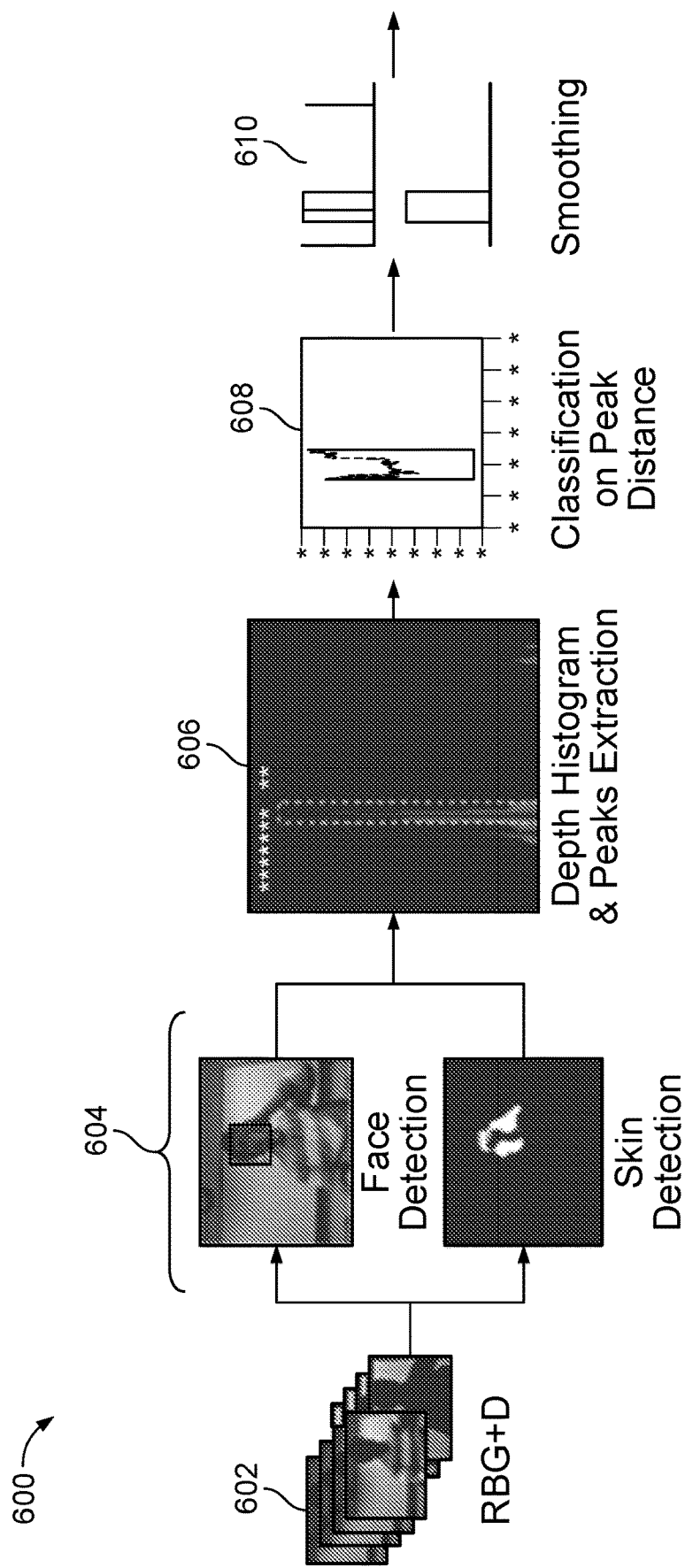
FIG. 6 shows an example pipeline for position classification
Figure 7:
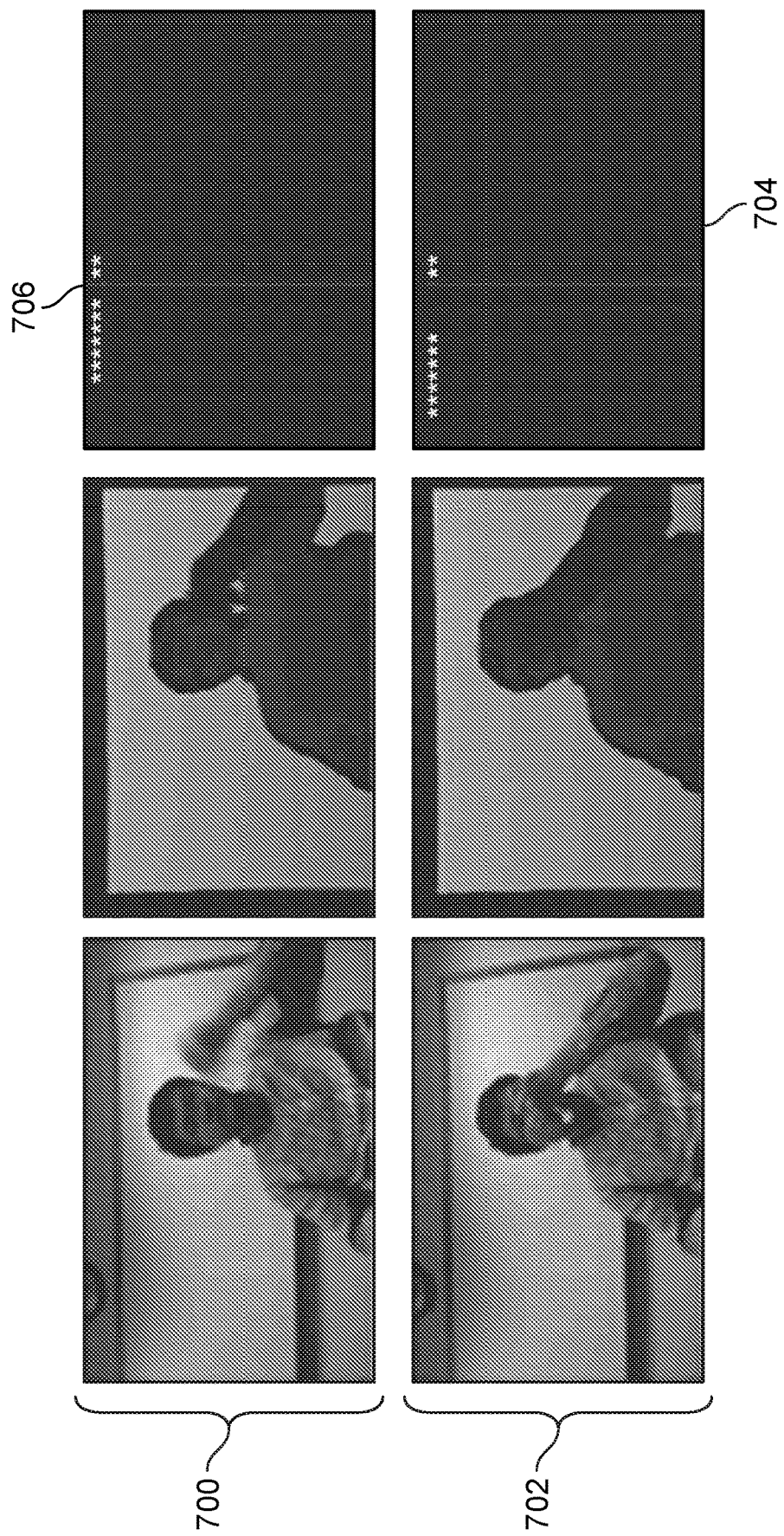
FIG. 7 shows depth histograms for a detected face region

The position classification pipeline 600 is depicted in FIG. 6. With the assumption that mouth and face naturally share a similar depth relative to the camera, face detection is utilized by the position classification engine 208 for positioning the mouth relative to the inhaler. In some implementations, a user's face is detected on the RGB image using Locally Assembled Binary (LAB) cascade face detector. The depth histogram of all the pixels is then computed in the detected bounding box filtered by skin color mask under HSV color space. Intuitively, the peak value of the histogram should correspond to the depth of the face, as shown in images 700, 702 of FIG. 7. To handle the problem of detecting faces in the RGB image with the hand in front, it is assumed that people do not move their heads significantly during positioning and consider the face area detected beforehand movement same as the area during positioning.

During positioning, two peaks are expected in the depth histogram after filtering the skin color: corresponding to face and hand, shown in image 704. To find the peaks, the histogram with multi-scale Gaussian and then perform normalization. Thresholds for identifying peaks (minimum probability of histogram) are then applied to extract first and the second global maximum. If the distance between the two peaks is less than the distance threshold $\theta_p$, it is considered as a valid inhaler position. The output of position checking is smoothed (610) by an alpha filter with smoothing factor $\alpha_p$.

Returning to FIG. 6, the position classification pipeline 600 is described. The position classification engine 208 is configured to receive (602) the image data comprising the series of images. For each image, the position classification engine 208 is configured to segment the image into a plurality of subsections, apply, to at least one subsection of the plurality of subsections, a plurality of binary classifiers to generate a classification vector for the at least one subsection, the classification vector indicating which binary classifiers are satisfied, and the plurality of binary classifiers indicating (604) that the face of the user or the inhaler is present in the at least one subsection, and compare (606) the classification vector to a threshold vector, wherein the subsection of the image includes the face of the user or the inhaler when values the classification vector satisfies the threshold vector. The position classification engine 208 is configured to retrieve a first range value associated with a first subsection comprising the face of the user in the image, retrieve a second range value associated with a second subsection comprising the inhaler in the image, and classify (608) peak distance between the user and the device. The position classification engine 208 is configured to output position data indicating that the position of the face of the user relative to the inhaler is correct when a difference between the first range value and the second range value is less than a predefined threshold difference. In some implementations, a smoothing operation (610) is performed.

Turning to exhale and puff detection, audio data are used by the audio classification engine 210 to detect these actions. This is because using visual cues to detect exhale, inhale and puff actions are difficult since there is no significant variation in RGB or depth data during these actions. Exhaling is naturally followed by inhaling after one cleans his lung. Therefore, in this task, exhaling and inhaling are considered as a pair, and so the data processing system 200 focuses on exhale detection.

Figure 8:
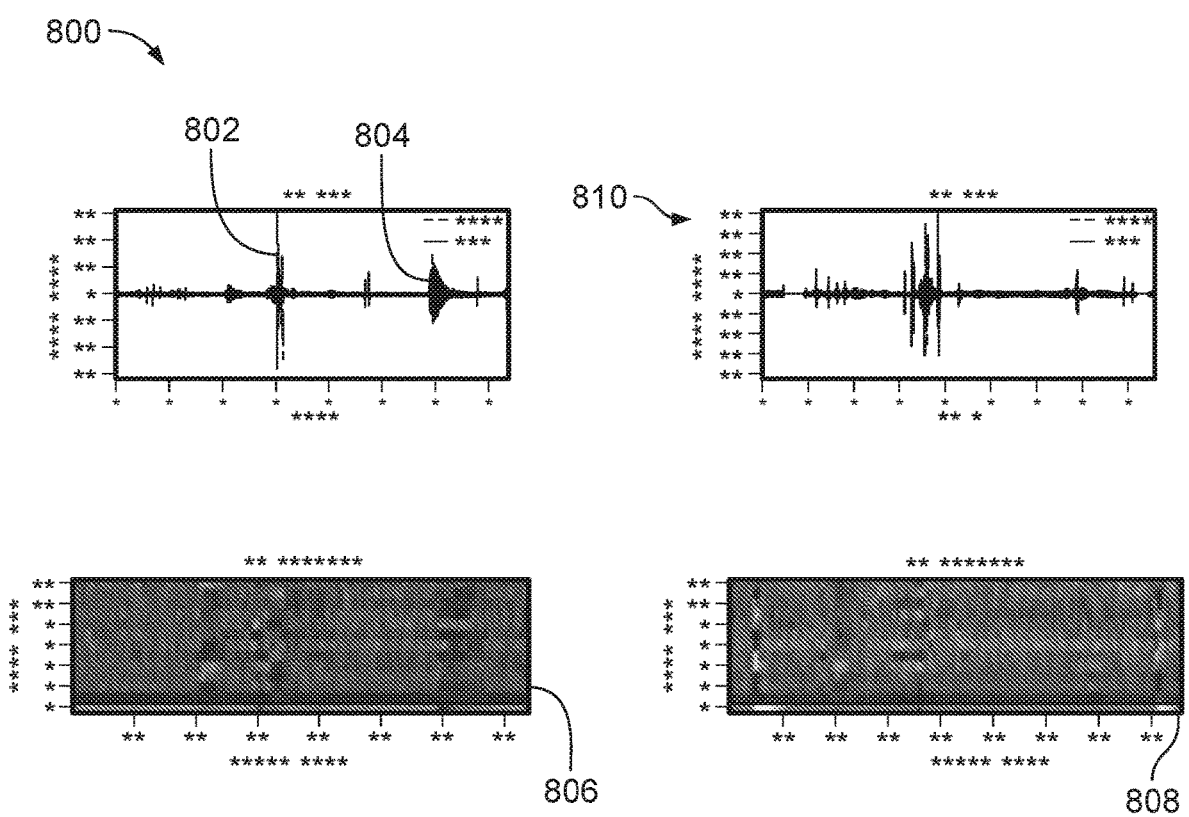
FIG. 8 shows example audio signals.

FIG. 8 shows two typical audio signals 800, 810 during inhalation and puff events. The ideal case is signal 800, in which the peak 802 is the puff sound and the triangle shape signal group 804 is the exhale sound. Signal 802 shows a much harder case. The user breathed out in such an ambiguous way that the events can hardly be differentiated from noise.

Figure 9:
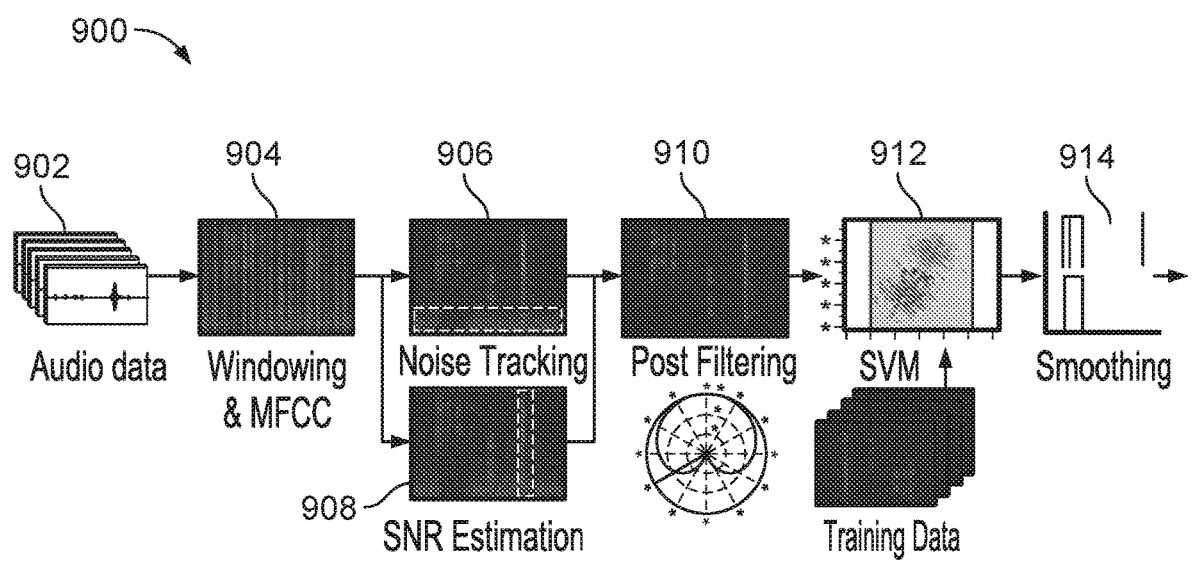
FIG. 9 shows an example pipeline for audio classification.

FIG. 9 shows a pipeline 900 for exhale and puff detection using audio by the audio classification engine 210. The audio signal is first down-sampled (902) to 16 KHz then framed (904) (a sliding Hamming window is used for windowing and the frame length/shift is 25/8 ms respectively). For each frame, a set of spectral features are extracted (906). Mel-frequency cepstrum coefficients (MFCCs) are widely used in speech recognition and audio event detection. MFCCs encode the short-time power spectrum of a sound, based on a linear cosine transform of a log power spectrum on a nonlinear mel scale of frequency. The MFCC feature used here is a 39-dimension vector. The first dimension is the energy component, and the rest of the 12 dimensions are the MFCC coefficients. After pre-processing for noise reduction, the feature vector is updated and concatenated 13-26th and 27-39th dimensions as its first and second order differential derivatives. In FIG. 8, images 806, 808 show the corresponding MFCC features for the example audio signals 800, 810.

Returning to FIG. 9, the reduction of background noise (such as air conditioner in the clinic or ground noise flow of the microphone) is a challenging but critical task to improve the robustness in speech recognition as well as audio event detection. In this task, noise tracking (906), signal to noise ratio (SNR) estimation (908) and post filtering techniques (910) are used to improve the classification accuracy. The audio signal s(t) is assumed to be degraded by an additive uncorrelated noise signal n(t).

$$y(t)=s(t)+n(t) \tag{1}$$

where t is the discrete time index. After MFCC, the corresponding spectrum is:

$$Y(n,k)=S(n,k)+N(n,k) \tag{2}$$

where n is the frame index and k is the band index. Statistical approaches to estimate power spectral density (PSD) of the noise signal is then applied to estimate noise PSD and SNR. There are many prominent approaches for the estimation such as using voice activity detector (VAD). For this task without human speech, a minimum statistics approach is applied by the audio classification engine to estimate the a-posteriori noise variance $\hat{\sigma}^2_N(n, k)$ after recording. The process is further described in R. Martin. Noise power spectral density estimation based on optimal smoothing and minimum statistics. IEEE Transactions on Speech and Audio Processing, 9(5):504-512, July 2001, incorporated herein in entirety by reference. The instantaneous SNR γ(n, k) then can be represented as:

$$\gamma(n, k) = \frac{Y(n, k)}{\hat{\sigma}^2_N(n, k)} \tag{3}$$

The actual post filtering is then performed by multiplying the noisy spectrum Y(n, k) with a weighting gain G(n, k) as:

$$S'(n,k)=G(n,k)Y(n,k) \tag{4}$$

Where G(n, k) is a function of noise PSD and SNR estimation. In this task we use Eq. 9 in T. Esch and P. Vary. Efficient musical noise suppression for speech enhancement system. In IEEE International Conference on Acoustics, Speech and Signal Processing (ICASSP), pages 4409-4412, April 2009, incorporated herein by reference in entirety. There are two main differences in the data processing system 200. First, since the audio data are first recorded, the minimum statistics are calculated under a complete audio span instead of clipping based. Second, with the four-channel audio recording by Kinect, generalized side-lobe cancellation (GSC) techniques in is applied to steer the spatial beam at the patient to further improve audio SNR.

Since the length in time of puffing and exhaling events are usually at the order of 100 ms, original 8 ms frame is too short to be discriminative. Additionally, there are many short-term variations within audio frame in practical recording. To relieve these side effects, consecutive N frames are collected as an audio clip and build the mean support vectors (MSVs) of audio signal by averaging the feature vectors in the frames of a clip:

$$V(m, k) = \frac{1}{N}\sum_i S'(n, k) \tag{5}$$

where m is the index of clip. Then the clips are trained and classified using multi-class SVM followed by alpha filtering with $\alpha_\alpha$ for smoothing.

In some implementations, the audio classification engine 210 performs the following actions. The audio classification engine 210 receives the audio data. The audio classification engine 210 encodes the audio data into a short-term power spectrum. The audio classification engine 210 estimates a noise component of the short-term power spectrum. The audio classification engine 210 filters the noise component from the short-term power spectrum to generate a filtered short-term power spectrum. The audio classification engine 210 applies support vector machine logic to the filtered short-term power spectrum. The audio classification engine 210 outputs a classification of the short-term power spectrum, the classification indicative of a likelihood that the audio data represents an inhalation sound of the user or a likelihood that the audio data represents a puff activation of the inhaler.

The audio classification 210 is assisted by temperature data 238 received from the temperature sensor 236. The temperature data 238 includes data indicating a temperature near the mouth of the user 240. Typically, the temperature near a mouth of the user 240 is relatively cooler when inhaling and relatively warmer when exhaling. Because the difference between exhaling and inhaling sounds can be difficult to detect by audio only, the temperature data 238 provides an additional means to classify the audio data 234 as representing an inhalation sound, an exhalation sound, and/or a puff sound as described above.

Recall that, proper inhaler technique requires the specific actions to be performed. One purpose of the system is to identify incorrect actions while using the inhaler and to report the problems to the patient to coach the patient to improve his/her techniques. In this section, we present a rule-based system to complete the coaching aspect of the present invention.

Figure 10:
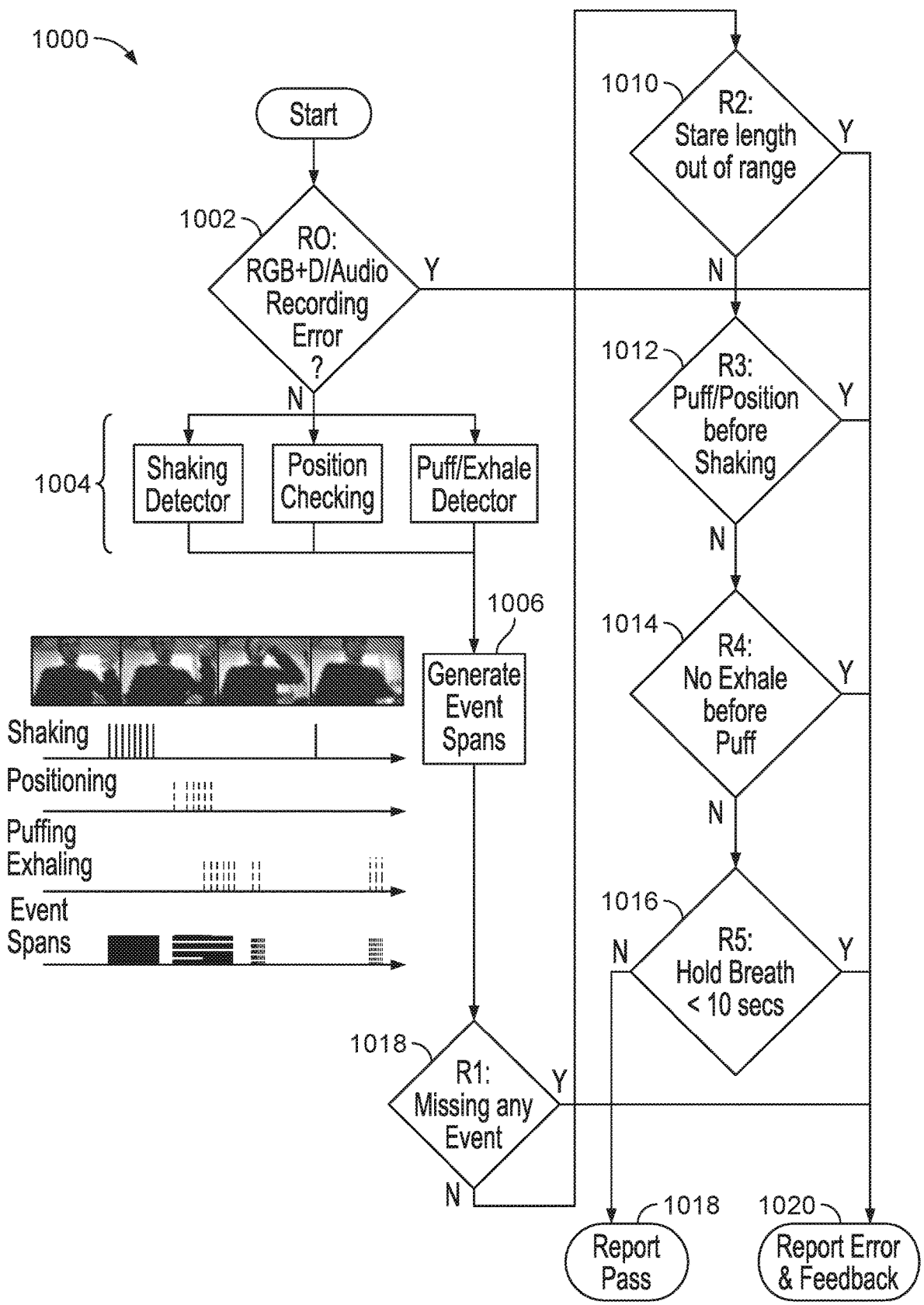
FIG. 10 shows an example process for providing rule-based inhaler device usage feedback.

The process 1000 of the rules logic engine 216 is shown in FIG. 10. The rules logic engine 216 ensures (1002) the quality of the recorded data. After Kinect records the patient's inhaler usage, the system first checks whether the RGB-D data is recorded under feasible position and distance (e.g., as depicted in FIG. 3). After 12 dB dynamic range control (DRC) of all microphone channels (same gain for all four audio channels), audio signals are checked in avoidance of clipping and blocking of microphones.

The rules logic engine 216 analyzes (1004) the recordings that pass the first check to evaluate and combine the classifier outputs for the shaking classifier engine 206, positioning classifier engine 208, and inhaling and puff actions of the audio classifier engine 210. Event spans can be generated (1006) which show the actions on a timeline (see FIG. 11).

The design of rules aims to cover standard guidelines and detect common mistakes. The first rule of the rules logic engine 216 checks (1008) whether the patient completes every step of using the inhaler device. If any step is missed, the rules logic engine 216 reports an error (e.g., an alert 244) and can provide instructions (e.g., a hint) to the user as to which action was missed. The second rule of the rules logic engine 216 checks (1010) lengths of actions to make sure every action is within a reasonable duration. Shaking an inhaler to mix the medication is required before putting it in front of the mouth and puffing. This sequence is checked (1012) by the first occurrence of shaking, positioning and puffing action. In addition, one of the most common mistakes of using inhaler is forgetting to exhale before puffing the medicine. The rules logic engine 216 checks (1014) whether the patient follows the correct order of exhaling and puffing. The rules logic engine 216 examines (1016) a 10-second breath-hold. In other words, the rules logic engine 216 checks the distance in time between puffing end and the following exhaling should be greater than 10 seconds. This step ensures adequate lung delivery.

The rules logic engine 216 process 1000 of coaching the user in real time is completed when all the rules are satisfied. As shown in FIG. 2C, if there is any violation of the rules, the patient will be informed with instructions accordingly. The data processing system 200 replays the video with guidelines for incorrect actions and encourage for correct actions at the time when an action takes place.

Experimental results of the data processing system 200 are discussed, below.

The entire dataset with 77 videos/audios is divided into 11 folds, each fold corresponding to one person. The count of an event, average distances in time (ms) between two events (e.g. shaking-end to position-start) and the average length of events (e.g. shaking-start to shaking-end) are summarized in Table 1.

TABLE 1

Event Statistics In Time (ms)

| event (counts) | shaking (64) | positioning (77) | puffing (68) | exhaling (104) |
|---|---|---|---|---|
| shaking (64) | 2284.3 | 3456.4 | 4948.9 | 2783.2 |
| positioning (77) | 3456.4 | 2685.1 | 1492.5 | 847.7 |
| puffing (68) | 4948.9 | 1492.5 | 314.3 | 2165.7 |
| exhaling (194) | 2783.2 | 847.7 | 2165.7 | 762.9 |

All evaluation results follow leave-one-person out cross-validation. Recall, precision and F1 are used to score for performance measurement. For evaluation of the present invention, two types of samples are of concern. The first one is the conventional discrete unit, which directly estimates the performance of a classifier. The ground truth labels are given for the unit, and the classifier output is compared with the truth to give a binary detection accuracy for a single unit. The unit selections are as follows: 5 frames for shaking and positioning and 10 frame clips (80 ms) for puffing and exhaling.

Analyzing usage of inhaler can be viewed as an event (shaking, positioning, puffing, exhaling) detection problem as in Human Activities Recognition and Localization competition (HARL). For monitoring and coaching inhaler usage, what is important is the spans (start time, end time, and duration) of different events and their relationships with each other. That is, the existence of events, and the order of event sequence are more critical to determine whether a patient use the inhaler correctly. For example, a miss or false alarm pulse at a specific time in puff detection is not very important. In contrast, a complete miss of puffing action span or puffing before shaking matters. For this purpose additional to the accuracies for the classifiers, additional evaluation metrics are defined for event detection.

Figure 11:
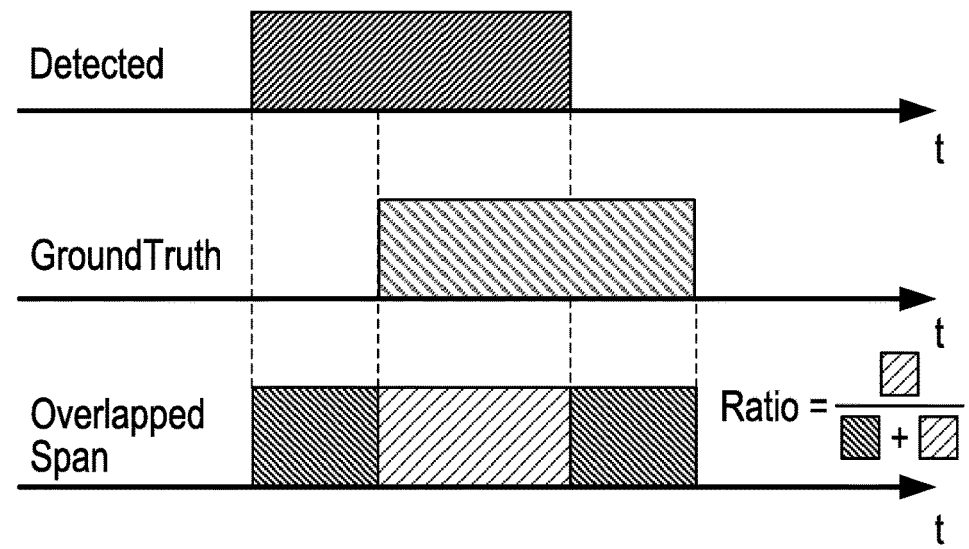
FIG. 11 shows an example of overlapped event spans.

As shown in FIG. 11, to find the outputs for spans, the tags of units are derived from the probability of the detector output and a threshold. Consecutive units of tags are merged into spans. To alleviate imperfect classification output, spans are being smoothed. Two spans are merged into one if the distance between them are less than two units. After merging spans, if a span last only one unit, this singular span will be removed.

Recall and precision for event detection based on spans are defined as follows:

$$\text{Recall}(G, D) = \frac{\sum_v \sum_a I(G^{a,v}, D^v)}{\sum_v |G^v|} \quad (6)$$

$$\text{Precision}(G, D) = \frac{\sum_v \sum_a I(D^v, G^{a,v})}{\sum_v |D^v|},$$

where $G^{a,v}$ corresponds to the $a^{th}$ action in the $v^{th}$ video in ground truth list. D indicates the detected list. The indicator function $I(X^{a,v}, Y^a)$ is defined as:

$$I(X^{a,v}, Y^v) = \left( \arg\max_{a'=1\ldots|Y^v|} \frac{X^{a,v} \cap Y^{a',v}}{X^{a,v} \cup Y^{a',v}} > \theta_a \right) \quad (7)$$

where $\theta_0$ is the overlap threshold. A simple example 1100 is shown in FIG. 11. Indicator function outputs 1 if the overlap ratio between detected and ground truth event is greater than $\theta_0$ and 0 otherwise.

Different scenarios in generating trajectory descriptors for detection of shaking action were evaluated. (x, y) locations are used for the trajectory points to generate a "bag of-words" representation of the trajectory shapes. As an alternative, statistics are used, i.e. mean and variance of these points. In addition, rather than use of normalized trajectories, the use of original positions is evaluated without normalization. The effect of length threshold was tested. In these evaluations, video clip (unit) size is set to w=5, trajectory tracking frames length is set to L=15, trajectory minimum length threshold is set to $\theta_l=100$, depth threshold is set to $\theta_d=80$, and the cluster size in the bag of words representation is set to K=100.

Figure 12:
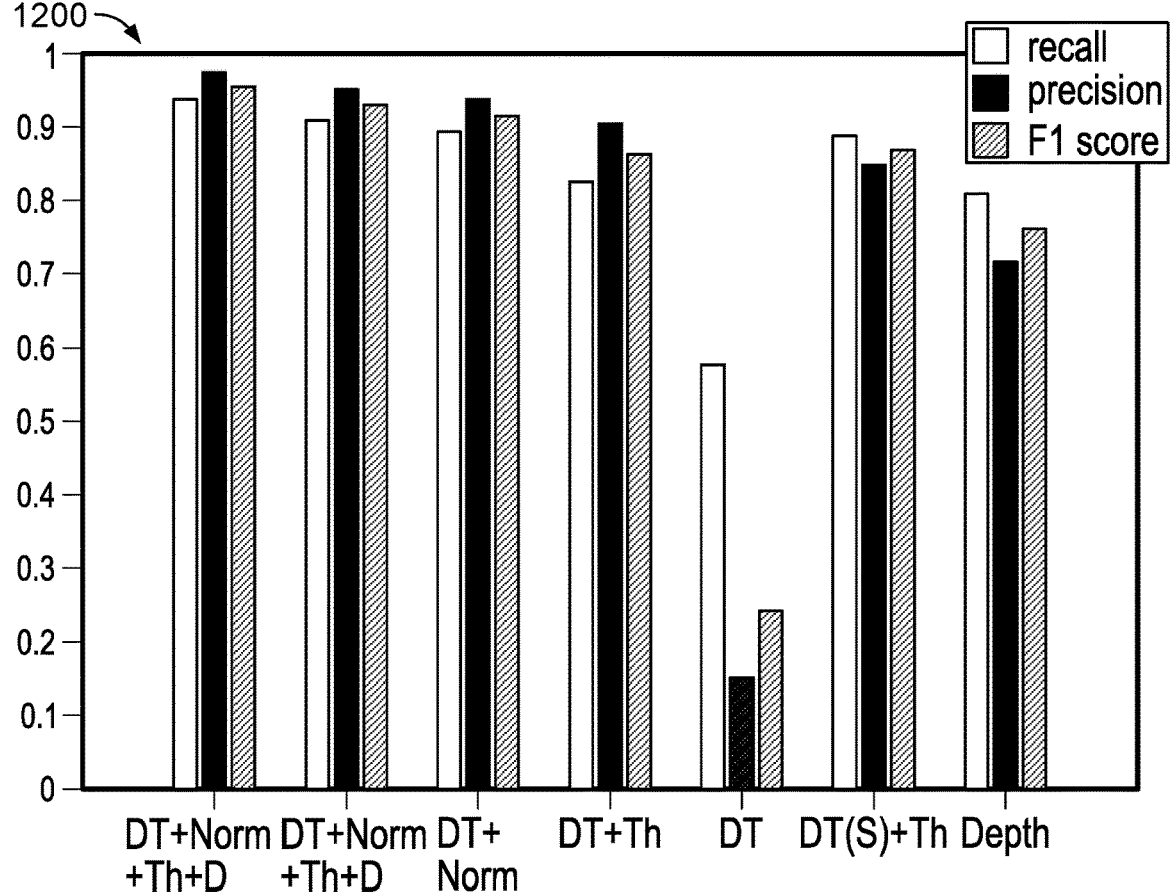

A shown in graph 1200 of FIG. 12, both normalized and non-normalized descriptors gain performance improvement by setting a length threshold (+Th), since the threshold can alleviate performance degradation from small body movements and random noises. Meanwhile, doing normalization (+Norm) improves the performance. Comparing with the full location descriptor (DT), statistics (S) cannot encode sufficient information for capturing the shape of trajectories. Note that, the proposed shaking detector achieves up to cross-validated 0.9153 recall, 0.9748 precision and 0.9442 F1 score.

The depth only approach was also tested where dense trajectories are extracted from a depth map. As seen in graph 1200, the results are worse than utilizing RGB (DT), and removal of the background using depth (+D) gives the best performance.

Recall that, the results above are based on classification accuracies on single units. We make use of the spans in order to test the effectiveness of an embodiment of the present invention in detecting events. The data processing system 200 considers an event as correctly detected if the overlap between the classified and ground truth spans is sufficiently large.

Graph 1300 of FIG. 13 implies that the proposed shaking detector is accurate in detecting shaking events for overlap threshold $\theta_0 <= 0.5$. For $\theta_0 = 0.5$, F1 score is 0.9922 while precision and 0.9844 recall 1.0000.

Figure 14B:
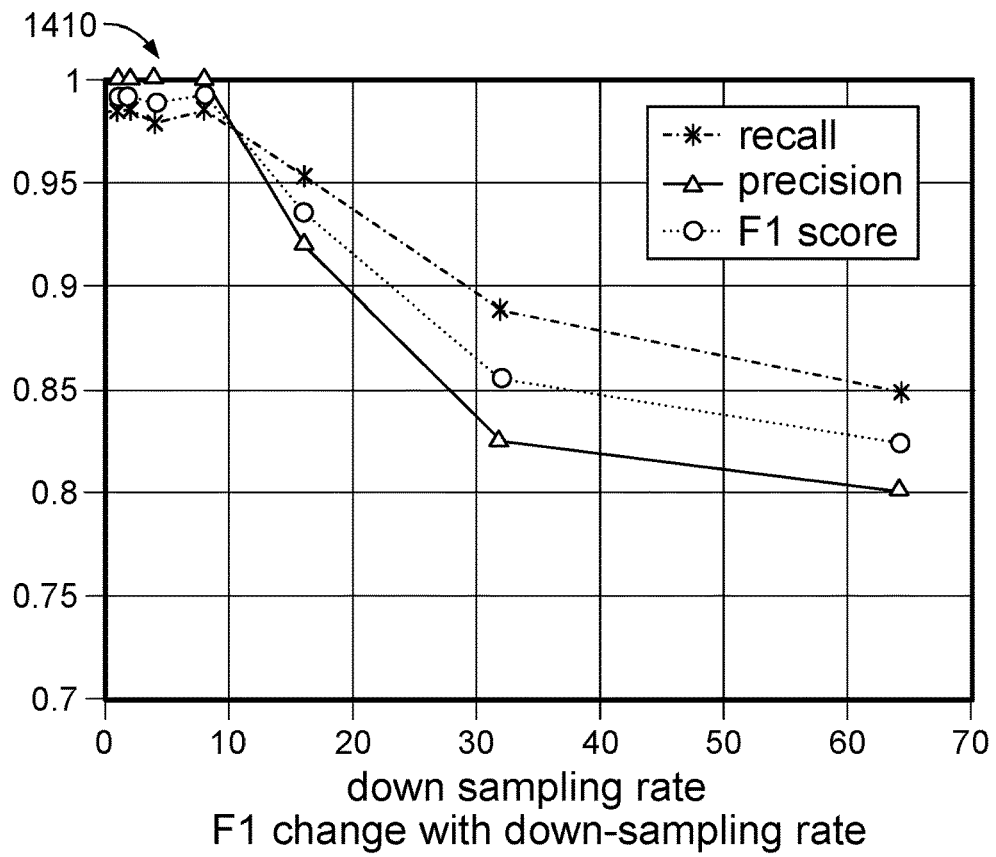

Fixing all the other parameters, the effect of varying the number of clusters K in codebook generation was evaluated. Graph 1400 of FIG. 14 shows the result under overlap rate $\theta_0 = 0.5$. Each K value represents the average performance of 20 times randomly initialized seeds in k-means. Generally, the performance drops as K increases due to overfitting, and best results for our dataset is achieved with K=100.

In order to expedite the feature extraction process for real-time application, one applicable approach is to trade-off between down-sampling rate and performance. In the down-sampling test, all frames are resized from 640×480 to 80×60 and compared under too=0.5. As shown in graph 1402, an 8-times down sampling does not decrease the overall accuracy, while it significantly improves the feature extraction speed. In contrast, rates greater than 8 cause unacceptable performance degrade. Using the original video frame size, 640×480, the dense trajectory extraction process is 11 times the real-time. After down sampling the video frame size to 80×60, with down-sample rate 8, the feature extraction only takes 0.25 of real-time. Under this speed, a real-time application for the shaking detection is built.

The premise of accurate position checking depends on a robust face detector. In the experiments, two different face detection methods are compared. The first is the Local Binary Pattern (LBP) cascade face detector used in the system and the other one is Locally Assembled Binary (LAB) cascade face detector. Each algorithm was testing with/without skin masking.

The data processing system 200 was tested with other possible options. The detector based on skeleton tracking utilized a tracking algorithm powered by NITE 1.5 for comparison. A positioning action is assumed if the position of the left or right hand joint is within a threshold $\theta_s$ to the position of the head joint.

Figure 15:
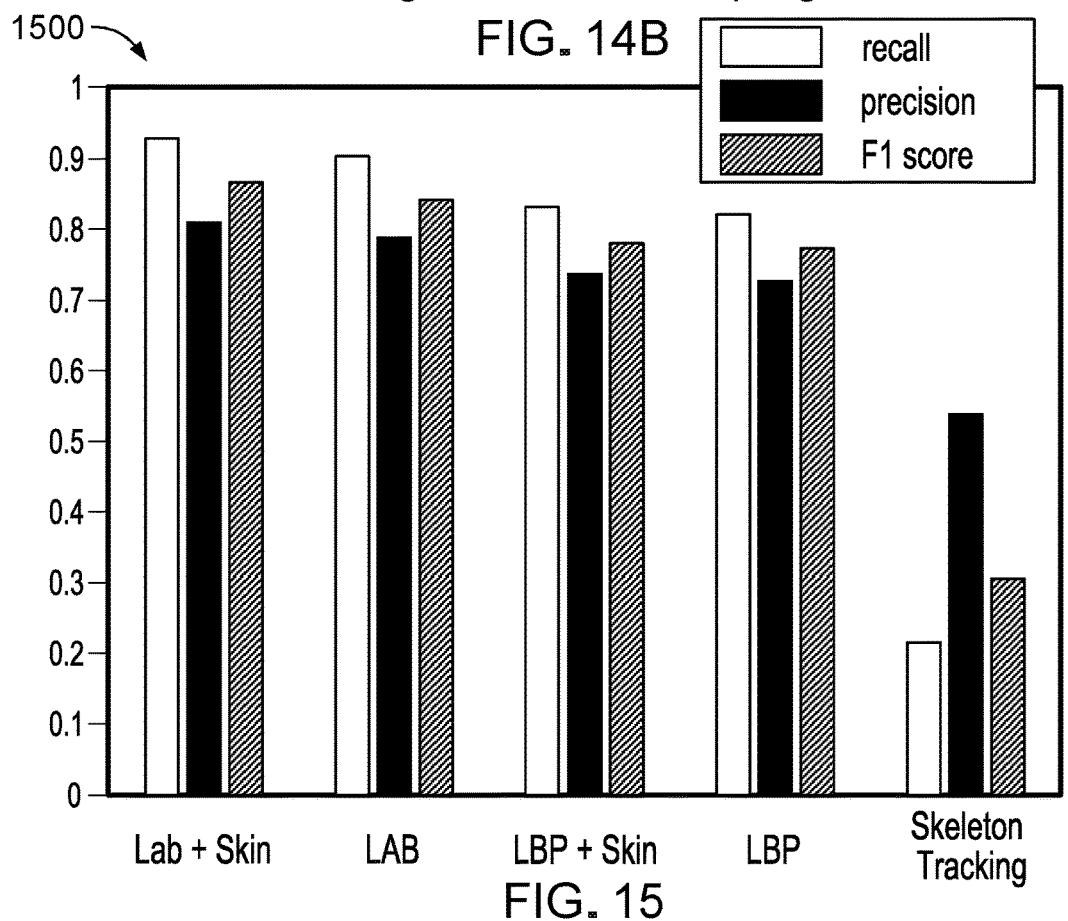

The results for unit classification shown in graph 1500 of FIG. 15 demonstrate that the proposed depth-histogram with skin altering method achieves highest F1 score. Skeleton tracking algorithm of NITE is not robust under the scenario depicted in FIG. 3 due to distance. In addition, skin altering also improves the performance. The best F1 score for the proposed position checking method is 0.8438 while the one for the LBP cascade face detector is 0.7556.

Figure 16:
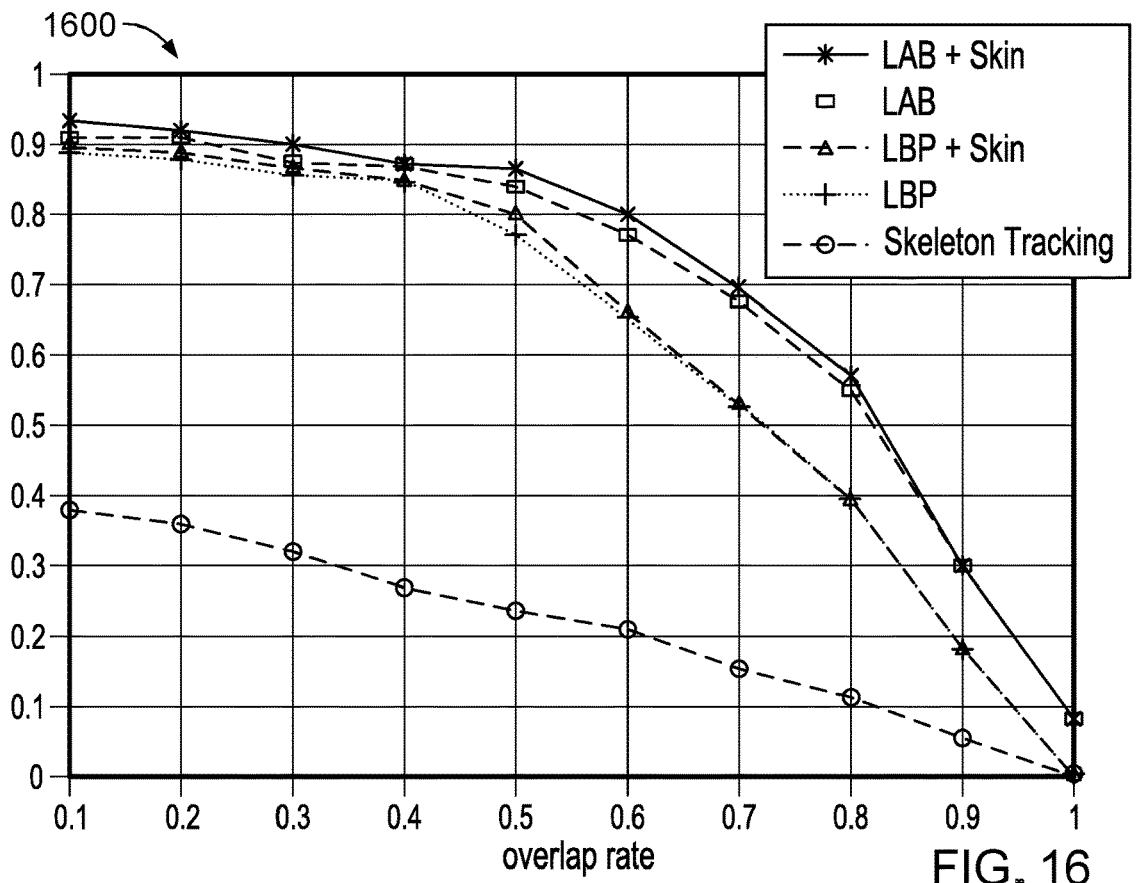
Figure 17:
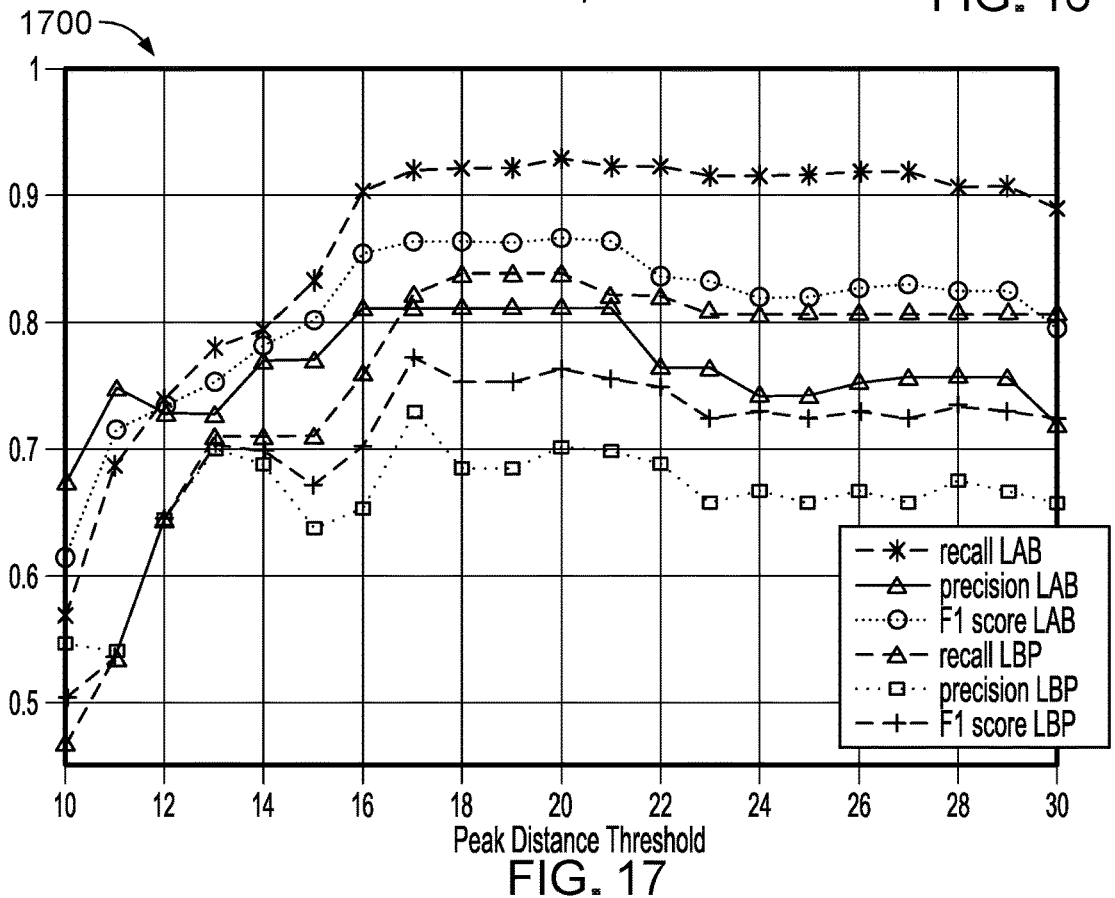

Graph 1600 FIG. 16 shows the event detection performance for different overlap ratios. The position checking event detection results with $\theta_0 = 0.5$ are depicted in graph 1700 of FIG. 17 for evaluating the distance threshold parameter $\theta_p$ between two peaks in normalized histogram. Experimental results indicates a threshold around 20 is better, which matches real world scenario (physically around two inches). The best F1 score for the proposed position checking method is 0.8666 under 0.5 overlap ratio, while the one for the LBP cascade face detector is 0.7933. The recall and precision of the proposed method are 0.9299 and 0.8114 respectively. In the error analysis of position checking, the lag in precision 0.8114 in comparison with shaking detector 0.9748 is mainly due to missed detection of face detector.

Figure 18:
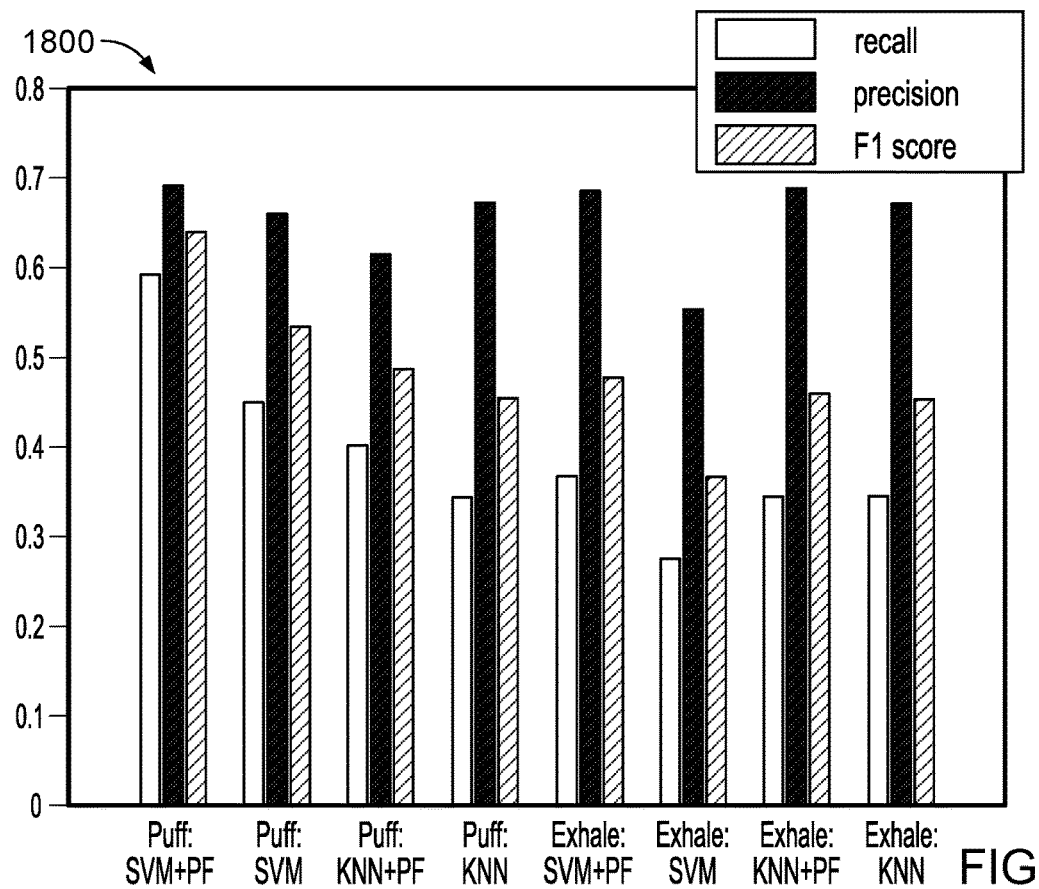
Figure 19:
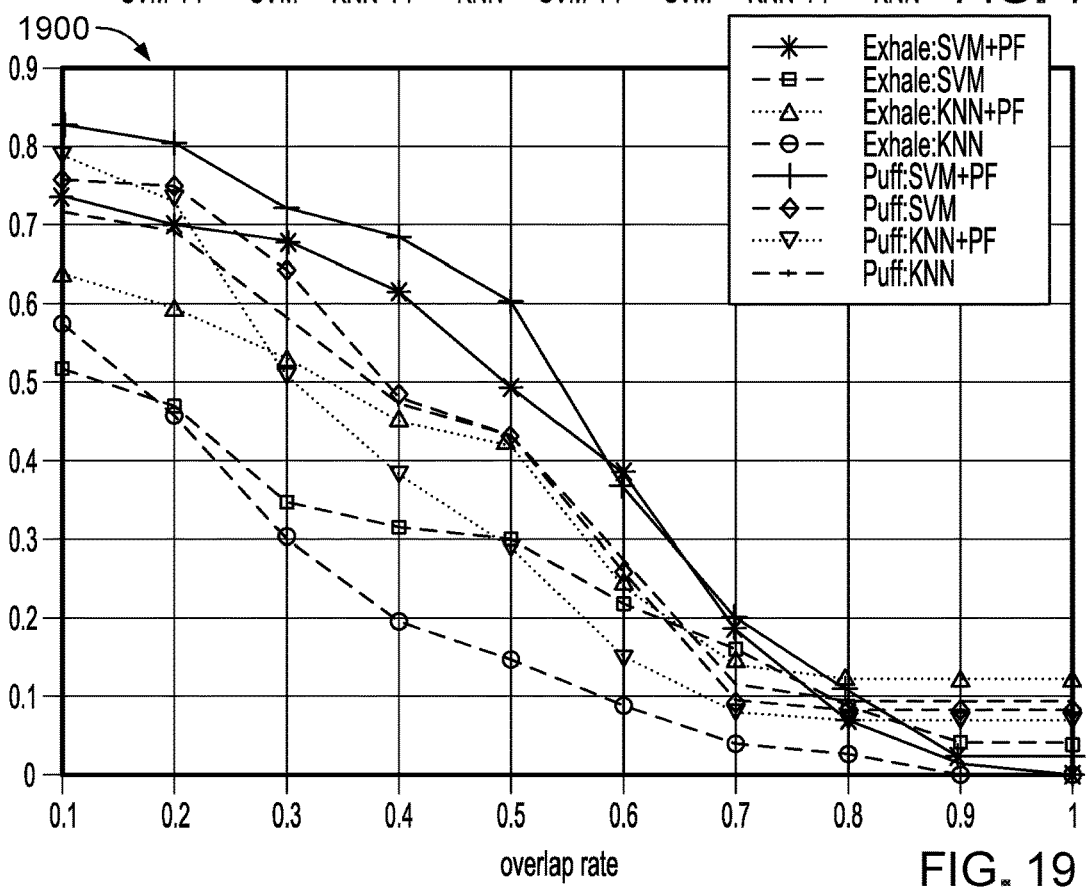

In comparison to shaking detection and position checking, puffing and exhaling detection is harder due to the lower audio SNR and indoor reverberant environment. To achieve better performance, pre-processing techniques are applied to suppress the noise via post filtering. The different learning methods are tested to determine their contributions on performance. A fine-tuned SVM approach was compared with K-nearest-neighbor (KNN). Graph 1800 of FIG. 18 and graph 1900 of FIG. 19 summarize the experimental results for unit and event detection respectively. The parameters of learning methods affect the performance dramatically.

Results are presented after parameter search and tuning. For SVM, the cost value set in the cost function is $\{1,2,5,8\} \times 10^{\{-1,0,1,2\}}$. Linear, RBF, and polynomial kernel were tested. $\gamma$ value (if applicable) set is $\{1,2,5,8\} \times 10^{\{-1,0,1,2\}}$ and degree value (if applicable) set is $\{1,2,3,5\}$. k in KNN is $\{3,5,15\}$.

The best result is achieved by SVM with degree 2 polynomial kernel and cost value c=5; $\gamma$=0.2. On the other hand, k=3 gives best KNN result.

For puffing detection, SVM with post filtering method achieves 0.6378 (clip), 0.6036 (event—with 0.5 overlap ratio). The best result for exhaling detection is 0.4805 (clip) and 0.4945 (event). The performance of exhaling detection, especially the recall rate, suffers from the distance between the patient and the sensing system (e.g., Kinect) as well as the nature of exhaling audio signal. In the error analysis, an exhaling event might be completely missed due to low SNR and combining other modalities such as but not limited to infrared data can improve detection.

The final system performance is summarized which combines all the classification results from shaking, positioning, puffing and exhaling detectors then jointly analyzes the patient's use of the inhaler. In the dataset, there are 14 negative ground truth examples (no improvement is required for the patient) and 63 positive examples (patients need instructions to improve their techniques).

Table 2 compares the best results of the proposed shaking, position checking, puffing and exhaling detectors under 0.5 span overlap ratio.

TABLE 2

Example performances of classifiers

| | Clip-based | | | Span-based $\theta_o$ = 0.5 | | |
|---|---|---|---|---|---|---|
| | Recall | Precision | F1 Score | Recall | Precision | F1 Score |
| Shaking | 0.9153 | 0.9748 | 0.9442 | 0.9844 | 1.0000 | 0.9922 |
| Positioning | 0.9219 | 0.7780 | 0.8438 | 0.9299 | 0.8114 | 0.8666 |
| Puffing | 0.5922 | 0.6932 | 0.6378 | 0.6623 | 0.5544 | 0.6036 |
| Exhaling | 0.3691 | 0.6882 | 0.4805 | 0.4327 | 0.5769 | 0.4945 |

For feedback purposes, one goal of the data processing system 200 is to identify improper techniques of a patient. Table 3 shows the results. The system achieves a high F1 score (0.9134) for this task. The results demonstrate great potential of the data processing system 200 in supporting doctors to improve the quality of health care service as well as coaching patients to develop proper inhaler techniques.

TABLE 3

Overall correctness of the rules based logic engine output

| | Recall | Precision | F1 Score |
|---|---|---|---|
| Coaching System (for correctness) | 0.5714 | 0.6154 | 0.5926 |
| Coaching System (for error) | 0.9063 | 0.9206 | 0.9134 |

While this specification contains many specific implementation details, these should not be construed as limitations on the scope of any invention or of what may be claimed, but rather as descriptions of features that may be specific to particular embodiments of particular devices. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can, in some cases, be excised from the combination, and the claimed combination may be directed to a sub combination or variation of a sub combination.

Particular embodiments of the subject matter have been described. Other embodiments are within the scope of the following claims. As one example, the processes depicted in the accompanying figures do not necessarily require the particular order shown, or sequential order, to achieve desirable results.

What is claimed is:

1. A data processing system for digitally processing live data feeds of inhaler device operation, the data processing system comprising:
   data storage configured to obtain, from one or more external data sources, a live data feed representing operation of an inhaler device, the live data feed including video data;
   a digital processing engine configured to:
      query, from the data storage, a live data feed representing, in the video data, a physical operation of an inhaler device,
      for a frame of the video data, sampling a portion of the frame, the portion of the frame corresponding to a position of the inhaler device in the frame
      determine, responsive to sampling the portion of the frame, a first value representing a change in a position of the inhaler device in the frame of the video data relative to another position of the inhaler device in another frame of the video data;
      determine, responsive to sampling the portion of the frame, a second value representing a position, of a user in the frame, relative to the inhaler device;
      generate a vector comprising at least the first value and the second value;
      apply a video classifier to the vector to classify the video data, the video classifier being trained with training data indicative of correct shaking of the inhaler; and
      based on the classified video data classified by the video classifier, output a prompt specifying whether operation of the inhaler device is within a threshold range of operation that indicates a correct shaking of the inhaler device.

2. The data processing system of claim 1, wherein the digital processing engine is further configured to:
   output-shake classification data indicative of a likelihood that the video data is indicative of the correct shaking of the inhaler.

3. The data processing system of claim 2, wherein the digital processing engine is further configured to:
   receive the video data;
   for each frame of the video data:
      segmenting the frame into a plurality of subsections;
      applying, to at least one subsection of the plurality of subsections, a plurality of binary classifiers, the plurality of binary classifiers indicating that the at least one subsection comprises a representation of a first anatomical feature face of the user or a second anatomical feature;
      retrieving a first range value associated with a first subsection comprising a representation of the first anatomical feature of the user in the frame;
      retrieving a second range value associated with a second subsection comprising a representation of the second anatomical feature of the user in the frame;
      determining that a difference between the first range value and the second range value is less than a threshold difference; and
      outputting position data indicating a likelihood that the inhaler is correctly positioned relative to the user.

4. The data processing system of claim 3, wherein the digital processing engine further is further configured to:
   receive audio data corresponding to the video data;
   encode the audio data into a power spectrum;
   estimate a noise component of the power spectrum;
   filter the noise component from the power spectrum to generate a filtered power spectrum;
   apply an audio classifier to the filtered power spectrum, the audio classifier being trained with training data indicative of one or more of an exhalation sound, an inhalation sound, and an inhaler puff sound; and
   responsive to applying the audio classifier, output audio classification data indicative of a likelihood that the audio data is indicative of the exhalation sound and a likelihood that the audio data is indicative of the inhaler puff sound.

5. The data processing system of claim 4, wherein the digital processing engine is further configured to:
   receive the audio classification data, the shake classification data, and the position data;
   based on the audio classification data, the shake classification data, and the position data, determine that the video data and the audio data represent a shake event, a position event, a puff event, and an exhalation event;
   determine an order for the shake event, the position event, the puff event, and the exhalation event; and
   responsive to determine that the order matches a predefined order of events, output data representing instructions for inhaler operation by the user.

6. The data processing system of claim 5, wherein the video classifier and the audio classifier each comprises a support vector machine.

7. The data processing system of claim 2, wherein the first value represents a trajectory value that is calculated using a dense trajectory feature.

8. The data processing system of claim 3, wherein the plurality of binary classifiers are a portion of a locally assembled binary (LAB) cascade face detector.

9. The data processing system of claim 4, wherein the power spectrum comprises a mel-frequency cepstrum.

10. The data processing system of claim 5, wherein shake classification, position classification, and audio classification operate in parallel and in real-time as the as the live data feed is obtained.

11. The data processing system of claim 5, wherein the digital processing engine is further configured to:
    determine that a time between the puff event and an additional exhalation event exceeds ten seconds; and responsive to determining that the time exceeds ten seconds, output data indicating correct usage of the inhaler by the user.

12. The data processing system of claim 5, further comprising:
a user interface configured to display the data representing instructions for inhaler operation by the user, the data comprising a status indicator for one or more of the shake event, the position event, the puff event, and the exhalation event, the status indicator for each respective event representing a pass or fail for the respective event.

13. The data processing system of claim 5, further comprising a user interface configured to display one or more instructions indicative of corrective action in response to a determination by the digital processing engine that the order does not match the predefined order of events or that one or more of the shake event, the position event, the puff event, and the exhalation event are not represented by the audio data and the video data.

14. The data processing system of claim 1, further comprising a camera for obtaining video data, a microphone for obtaining audio data, and a ranging sensor for obtaining range values, wherein outputting the prompt is based on the video data, the audio data, and range values.

15. The data processing system of claim 1, further comprising a temperature sensor for obtaining temperature data, wherein outputting the prompt is based on the obtained temperature data.

16. A method for classification of data representing a plurality of inhaler operations, the method comprising:
obtaining, by an data storage from one or more external data sources, a live data feed representing operation of an inhaler device, the live data feed including video data;
querying, by a digital processing engine, from the data storage, a live data feed representing, in the video data, a physical operation of an inhaler device;
for a frame of the video data, sampling a portion of the frame, the portion of the frame corresponding to a position of the inhaler device in the frame
determining, responsive to sampling the portion of the frame, a first value representing a change in a position of the inhaler device in the frame of the video data relative to another position of the inhaler device in another frame of the video data;
determining, responsive to sampling the portion of the frame, a second value representing a position, of a user in the frame, relative to the inhaler device;
generating a vector comprising at least the first value and the second value;
apply a video classifier to the vector to classify the video data, the video classifier being trained with training data indicative of correct shaking of the inhaler; and
based on the classified video data classified by the video classifier, outputting a prompt specifying whether operation of the inhaler device is within a threshold range of operation that indicates a correct shaking of the inhaler device.

17. The method of claim 16, further comprising:
outputting shake classification data indicating a likelihood that the video data is indicative of the correct shaking of the inhaler.

18. The method of claim 17, further comprising:
for each frame of the video data:
segmenting the frame into a plurality of subsections;
applying, to at least one subsection of the plurality of subsections, a plurality of binary classifiers, the plurality of binary classifiers indicating that the at least one subsection comprises a representation of a first anatomical feature face of the user or a second anatomical feature;
retrieving a first range value associated with a first subsection comprising a representation of the first anatomical feature of the user in the frame;
retrieving a second range value associated with a second subsection comprising a representation of the second anatomical feature of the user in the frame;
determining that a difference between the first range value and the second range value is less than a threshold difference; and
outputting position data indicating a likelihood that the inhaler is correctly positioned relative to the user.

19. The method of claim 18, further comprising:
receiving audio data corresponding to the video data;
encoding the audio data into a power spectrum;
estimating a noise component of the power spectrum;
filtering the noise component from the power spectrum to generate a filtered power spectrum;
applying an audio classifier to the filtered power spectrum, the audio classifier being trained with training data indicative of one or more of an exhalation sound, an inhalation sound, and an inhaler puff sound; and
responsive to applying the audio classifier, outputting audio classification data indicative of a likelihood that the audio data is indicative of the exhalation sound and a likelihood that the audio data is indicative of the inhaler puff sound.

20. A data processing system configured for parallel classification of data representing a plurality of inhaler operations, the data processing system comprising:
a shake classification engine configured to classify image data, wherein the image data comprises a series of images representing a shaking operation of an inhaler, the shake classification engine configured to:
receive the image data comprising the series of images;
perform a thresholding operation on an initial image of the series of images to identify one or more features in the initial image;
sample the initial image at the one or more features to obtain a plurality of feature points, each feature point comprising data indicating a location of that feature point in the initial image;
for each feature point of the plurality, generate a trajectory vector by:
determining a location of the feature point in a next image in the series of images;
determining a displacement value between the location in the initial image of the feature point and the location of the feature point in the next image;
adding the displacement value to a total displacement value representing the trajectory vector; and
replacing the initial image with the next image;
wherein the displacement value is determined for each subsequent image in the series of images and added to the total displacement value;
generate a code vector representing the generated trajectory vectors, the code vector configured for inputting into support vector machine logic of the shake classification engine;

output, by the support vector machine logic, a classification of the code vector, the classification indicative of a likelihood that the shaking operation of the inhaler is correct;

a position classification engine configured to further classify the image data, wherein the image data comprises images representing a position of a face of a user relative to the inhaler, the position classification engine configured to:

receive the image data comprising the series of images;

for each image:
   segmenting the image into a plurality of subsections;
   applying, to at least one subsection of the plurality of subsections, a plurality of binary classifiers to generate a classification vector for the at least one subsection, the classification vector indicating which binary classifiers are satisfied, and the plurality of binary classifiers indicating that the face of the user or the inhaler is present in the at least one subsection;
   compare the classification vector to a threshold vector, wherein the subsection of the image includes the face of the user or the inhaler when values the classification vector satisfies the threshold vector;
   retrieve a first range value associated with a first subsection comprising the face of the user in the image;
   retrieve a second range value associated with a second subsection comprising the inhaler in the image;
   output position data indicating that the position of the face of the user relative to the inhaler is correct when a difference between the first range value and the second range value is less than a predefined threshold difference;

an audio classification engine configured to classify audio data, the audio classification engine configured to:
   receive the audio data;
   encode the audio data into a short-term power spectrum;
   estimate a noise component of the short-term power spectrum;
   filter the noise component from the short-term power spectrum to generate a filtered short-term power spectrum;
   apply support vector machine logic to the filtered short-term power spectrum;
   output a classification of the short-term power spectrum, the classification indicative of a likelihood that the audio data represents an inhalation sound of the user or a likelihood that the audio data represents a puff activation of the inhaler; and a rules logic engine configured to:
   receive the classification of the code vector, the position data, and the classification of the short-term power spectrum;
   apply a threshold to the classification of the code vector, the position data, and the classification of the short-term power spectrum;
   determine, responsive to applying the threshold, that each of a shaking event, a puff event, a position event, and an exhaling event are represented in the image data and the audio data;
   determine that an order of the shaking event, the puff event, the position event, and the exhaling event matches a predefined order; and
   in response determining that the order matches the predefined order, output data indicating that the user is correctly using the inhaler.

* * * * *

UNITED STATES PATENT AND TRADEMARK OFFICE
CERTIFICATE OF CORRECTION

| | | |
|---|---|---|
| PATENT NO. | : 11,676,713 B2 | Page 1 of 1 |
| APPLICATION NO. | : 16/769934 | |
| DATED | : June 13, 2023 | |
| INVENTOR(S) | : Po-yao Huang and Alexander G. Hauptmann | |

It is certified that error appears in the above-identified patent and that said Letters Patent is hereby corrected as shown below:

In the Specification

Column 1, Line 12, delete "2018" and insert -- 2018, --

In the Claims

Column 22, Line 20, Claim 4, after "engine" delete "further"

Column 22, Line 62, Claim 10, delete "as the as the" and insert -- as the --

Signed and Sealed this
Ninth Day of December, 2025

John A. Squires
*Director of the United States Patent and Trademark Office*